United States Patent
Khandekar et al.

(10) Patent No.: US 12,234,293 B2
(45) Date of Patent: Feb. 25, 2025

(54) TREATMENT FOR PRIMARY AMYLOIDOSIS WITH ANTI-BCMA BINDING PROTEIN

(71) Applicant: GLAXOSMITHKLINE INTELLECTUAL PROPERTY DEVELOPMENT LIMITED, Stevenage (GB)

(72) Inventors: Sanjay Khandekar, Collegeville, PA (US); Patrick Mayes, Devon, PA (US); Joanna Opalinska, Collegeville, PA (US)

(73) Assignee: GlaxoSmithKline Intellectual Property Development Limited, Stevenage (GB)

( * ) Notice: Subject to any disclaimer, the term of this patent is extended or adjusted under 35 U.S.C. 154(b) by 130 days.

(21) Appl. No.: 17/846,950

(22) Filed: Jun. 22, 2022

(65) Prior Publication Data

US 2023/0019140 A1    Jan. 19, 2023

Related U.S. Application Data

(62) Division of application No. 16/646,836, filed as application No. PCT/IB2018/056967 on Sep. 12, 2018, now Pat. No. 11,401,334.

(60) Provisional application No. 62/558,575, filed on Sep. 14, 2017.

(51) Int. Cl.
| | |
|---|---|
| *A61K 39/395* | (2006.01) |
| *A61K 31/573* | (2006.01) |
| *A61K 31/69* | (2006.01) |
| *A61K 47/68* | (2017.01) |
| *A61P 35/00* | (2006.01) |
| *C07K 16/28* | (2006.01) |
| *C07K 16/30* | (2006.01) |
| *C07K 19/00* | (2006.01) |
| *A61K 39/00* | (2006.01) |
| *C07K 14/71* | (2006.01) |

(52) U.S. Cl.
CPC ........ *C07K 16/2878* (2013.01); *A61K 31/573* (2013.01); *A61K 31/69* (2013.01); *A61K 39/3955* (2013.01); *A61K 39/39558* (2013.01); *A61K 47/6817* (2017.08); *A61P 35/00* (2018.01); *C07K 16/2896* (2013.01); *C07K 16/30* (2013.01); *C07K 19/00* (2013.01); *A61K 2039/505* (2013.01); *A61K 2039/545* (2013.01); *C07K 2317/56* (2013.01); *C07K 2317/76* (2013.01); *C07K 2317/92* (2013.01); *C07K 2319/55* (2013.01)

(58) Field of Classification Search
CPC .......... A61K 2039/505; A61K 39/3955; A61K 39/39558; A61K 2039/80; C07K 14/705; C07K 14/70596; C07K 14/70578; C07K 16/2878; C07K 16/2896; C07K 2317/56; C07K 2317/565; C07K 2319/00; C07K 2319/55; C07K 19/00; C07K 16/30
See application file for complete search history.

(56) References Cited

U.S. PATENT DOCUMENTS

| | | |
|---|---|---|
| 9,273,141 B2 | 3/2016 | Algate et al. |
| 2013/0280280 A1 | 10/2013 | Algate et al. |
| 2014/0105915 A1 | 4/2014 | Algate et al. |
| 2016/0297885 A1 | 10/2016 | Kuo et al. |
| 2019/0352427 A1* | 11/2019 | Vu .................... C07K 16/2809 |

FOREIGN PATENT DOCUMENTS

WO    2017093942 A1    6/2017

OTHER PUBLICATIONS

Driscoll et al. "Proteasome Inhibitors to Treat AL Amyloidosis". Exploring New Findings on Amyloidosis, InTech, Aug. 24, 2016. Crossref, doi: 10.5772/63467.*
Montes de Orca et al. Belantamab Mafodotin (GSK2857916) Drives Immunogenic Cell Death and Immune-mediated Antitumor Responses In Vivo. Mol Cancer Ther 20: 1941-1955, 2021.*
Paul, William E., Fundamental Immunology, 3rd Edition, Raven Press, New York, Chapt. 8, pp. 292-295 (1993).*
Rudikoff et al. Single amino acid substitution altering antigen-binding specificity. Proc Natl Acad Sci USA 79: 1979-1983, 1982.*
Vasudevan et al. A single amino acid change in the binding pocket alters specificity of an anti-integrin antibody AP7.4 as revealed by its crystal structure. Blood Cells Mol Diseases 32: 176-181, 2004.*
Zhang et al. Comprehensize optimization of a single-chain variable domain antibody fragment as a targeting ligand for a cytotoxic nanoparticle. mAbs 7(1): 42-52, 2015.*
Anonymous, "Study NCT03544281 on Date: May 23, 2018 (v1), To Evaluate Safety, Tolerability, and Clinical Activity of the Antibody-drug Conjugate, GSK2857916 Administered in Combination With Lenalidomide Plus Dexamethasone (Arm A), or in Combination With Bortezomib Plus Dexamethasone (Arm B) in Subjects With Rel", ClinicalTrials.gov archive, May 23, 2018 (May 23, 2018), XP055532114, Retrieved from Internet: URL:https://clinicaltrials.gov/ct2/history/NCT03544281?V 1=View#StudyPageTop [retrieved on Dec. 10, 2018] whole document, especially pp. 2, 4, 6, (10.
Podar et al., "Current and developing synthetic pharmacotherapy for treating relapsed/refractory multiple myeloma", Expert Opinion on Pharmacotherapy, vol. 18, No. 11, pp. 1061-1079 (2017).
Tai et al., "Targeting B-cell maturation antigen in multiple myeloma", Immunotherapy, Future Medicine, vol. 7, No. 11, pp. 1187-1199 (2015).

(Continued)

*Primary Examiner* — Bridget E Bunner
(74) *Attorney, Agent, or Firm* — Carly Shanahan

(57) ABSTRACT

Disclosed herein is a method of treating cancer, such as multiple myeloma, involving the combination of an anti-BCMA antigen binding protein (e.g., an anti-BCMA antibody) and a proteasome inhibitor (e.g. bortezomib). The combinations can also include an anti-inflammatory compound (e.g. dexamethasone).

19 Claims, No Drawings

Specification includes a Sequence Listing.

(56) References Cited

OTHER PUBLICATIONS

Alley et al., "Antibody-drug conjugates: targeted drug delivery for cancer," Curr Opin Chem Biol 14: 529-537, 2010.
Brorson et al., "Mutational analysis of avidity and fine specificity of anti-levan antibodies," J Immunol 163: 6694-6701, 1999.
Brummell et al., "Probing the combining site of an anti-carbohydrate antibody by saturation-mutagenesis: role of the heavy-chain CDR3 residues," Biochem 32(4): 1180-1187, 1993 (abstract).
Burks et al., "In vitro scanning saturation mutagenesis of an antibody binding pocket," Proc Natl Acad Sci USA 94: 412-417, 1997.
Cohen et al., "First in human study with GSK2857916, an antibody drug conjugated to microtubule-disrupting agent directed against B-cell maturation antigen (BCMA) in patients with relapsed/refractory multiple myeloma (MM): results from study BMA117159 part 1 dose escalation," Blood 128(22): 1148, 2016.
Colman et al., "Effects of amino acid sequence changes on antibody-antigen interactions," Res Immunol 145: 33-36, 1994.
Dimopoulos et al., "Carfilzomib and dexamethasone versus bortezomib and dexamethasone for patients with relapsed or refractory multiple myeloma (ENDEAVOR): a randomised, phase 3, open-label, multicentre study," Lancet Oncol 17: 27-38, 2016.
Dolloff et al., "Emerging therapeutic strategies for overcoming proteasome inhibitor resistance," Adv Cancer Res 127: 191-226, 2015.
Harrison et al., "The addition of dexamethasone to bortezomib for patients with relapsed multiple myeloma improves outcome but ongoing maintenance therapy has minimal benefit," Am J Hematol 90: E86-E91, 2015.
Jang et al., "The structural basis for DNA binding by an anti-DNA autobody," Mol Immunol 35: 1207-1217, 1998.
Kobayashi et al., "Tryptophan H33 plays an important role in pyrimidine (6-4) pyrimidone photoproduct binding by a high-affinity antibody," Protein Engineering 12(10): 879-884, 1999.
Mohan et al., "Update on the optimal use of bortezomib in the treatment of multiple myeloma," Cancer Management Res 9: 51-63, 2017.
Sutherland et al., "Lysosomal trafficking and cysteine protease metabolism confer target-specific cytotoxicity by peptide-linked anti-CD30 auristatin conjugates," J Biol Chem 281(15): 10540-10547, 2006.
Tai et al., "Novel anti-B-cell maturation antigen antibody-drug conjugate (GSK2857916) selectively induces killing of mutiple myeloma," Blood 123(20): 3128-3138, 2014.
Bross et al., "Approval summary for bortezomib for injection in the treatment of multiple myeloma," Clin. Cancer Res. 3954-3964 (2004).
Kamishohara et al., "Development of Novel Therapeutics for Multiple Myeloma and Improvement of Drug Lag," Nippon Rinsho, vol. 74, Extra No. 5, (2016), pp. 585-591.

\* cited by examiner

TREATMENT FOR PRIMARY AMYLOIDOSIS WITH ANTI-BCMA BINDING PROTEIN

CROSS REFERENCE TO RELATED APPLICATIONS

This application is a divisional of U.S. patent application Ser. No. 16/646,836, filed 12 Mar. 2020, which is a 371 of International Application No. PCT/IB2018/056967, filed 12 Sep. 2018, which claims the benefit of U.S. Provisional Application No. 62/558,575, filed 14 Sep. 2017, which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jun. 22, 2022, is named 054624-09-5014-US01_PU66428_US_Sequence_Listing.txt and is 10,000 bytes in size.

FIELD OF THE INVENTION

The present invention relates to methods of treating cancer in a subject. In particular, the present invention relates to a combination of an anti-BCMA antigen binding protein and a proteasome inhibitor for treating cancer. Combinations may further include an anti-inflammatory compound, such as dexamethasone.

BACKGROUND TO THE INVENTION

Multiple myeloma (MM) is an incurable malignancy and accounts for 1% of all cancers and for 10% of all hematologic malignancies. A variety of drugs and combination treatments have been evaluated and found effective in treating multiple myeloma (National Comprehensive Cancer Network, 2016; Moreau, San Miguel et al., 2017). However, most, if not all, of these patients inevitably relapse (Richardson, Barlogie et al., 2003; Richardson, Barlogie et al., 2006; Jagannath, Barlogie et al., 2008).

Three and four-drug combinations are emerging for patients with previously treated MM but these regimens may be limited by toxic effects (National Comprehensive Cancer Network, 2016). Agents with new mechanisms of action that can be combined with existing therapies without an increase in serious toxicity are needed. Therefore, there is an urgent need to develop treatment combinations with mechanism of action that do not overlap, and where cross-resistance with prior treatments could be minimized.

SUMMARY OF THE INVENTION

The disclosure relates to methods of treating cancer in a subject, e.g. a human. In particular, the present invention relates to a combination of an anti-BCMA antigen binding protein, such as an antibody, and proteasome inhibitor for treating cancer. Combinations may further include an anti-inflammatory compound such as dexamethasone. In one embodiment, the cancer is selected from multiple myeloma, chronic lymphocytic leukemia, and non-Hodgkin's lymphoma.

Provided herein is a method of treating cancer in a subject in need thereof comprising administering a therapeutically effective dose of a combination comprising an anti-BCMA antigen binding protein and proteasome inhibitor. In one embodiment, the combination further comprises an anti-inflammatory compound.

Also provided herein is a method of treating cancer in a subject in need thereof comprising administering a therapeutically effective dose of a combination comprising an anti-BCMA antigen binding protein and proteasome wherein the antibody comprises a CDRH1 comprising an amino acid sequence with at least 90% sequence identity to the amino acid sequence set forth in SEQ ID NO:1; a CDRH2 comprising an amino acid sequence with at least 90% sequence identity to the amino acid sequence set forth in SEQ ID NO:2; a CDRH3 comprising an amino acid sequence with at least 90% sequence identity to the amino acid sequence set forth in SEQ ID NO:3; a CDRL1 comprising an amino acid sequence with at least 90% sequence identity to the amino acid sequence set forth in SEQ ID NO:4; a CDRL2 comprising an amino acid sequence with at least 90% sequence identity to the amino acid sequence set forth in SEQ ID NO:5; and a CDRL3 comprising an amino acid sequence with at least 90% sequence identity to the amino acid sequence set forth in SEQ ID NO:6.

Further provided herein is a method of treating cancer in a subject in need thereof comprising administering a therapeutically effective dose of a combination comprising an anti-BCMA antigen binding protein and a proteasome inhibitor, wherein the anti-BCMA antigen binding protein is an antibody comprising a VH comprising an amino acid sequence with at least 90% sequence identity to the amino acid sequence set forth in SEQ ID NO:7; and a VL comprising an amino acid sequence with at least 90% sequence identity to the amino acid sequence set forth in SEQ ID NO:8.

Provided herein is a method of treating cancer in a subject in need thereof comprising administering a therapeutically effective dose of a combination comprising an anti-BCMA antigen binding protein, a proteasome inhibitor, and an anti-inflammatory compound, wherein the anti-inflammatory compound is dexamethasone.

Also provided herein is a method of treating cancer in a subject in need thereof comprising administering a therapeutically effective dose of a combination comprising an anti-BCMA antigen binding protein and a proteasome inhibitor, wherein the proteasome inhibitor is bortezomib. In another embodiment, the proteasome inhibitor is carfilzomib. In yet another embodiment, the proteasome inhibitor is ixazomib. In yet another embodiment, the proteasome inhibitor is oprozomib.

Further provided herein is a method of treating cancer in a subject in need thereof comprising administering a therapeutically effective dose of a combination comprising an anti-BCMA antigen binding protein and a proteasome inhibitor, wherein the anti-BCMA antigen binding protein is an immunoconjugate comprising an antibody conjugated to a cytotoxin. In one embodiment, the cytotoxin is MMAE or MMAF.

Provided herein is a method of treating cancer, wherein 1.9 mg/kg, 2.5 mg/kg, or 3.4 mg/kg of an anti-BCMA antigen binding protein is administered on day 1 of a 21-day cycle.

Further provided herein is a method of treating cancer, wherein the proteasome inhibitor is bortezomib and wherein 1.3 $mg/m^2$ of bortezomib is administered on days 1, 4, 8, and 11 of a 21-day cycle.

Also provided is a method of treating cancer, wherein the anti-inflammatory compound is dexamethasone and wherein 20 mg of dexamethasone is administered on days 1, 2, 4, 5, 8, 9, 11, and 12 of a 21-day cycle.

Provided herein is a combination for use in the treatment of cancer, wherein the combination comprises an anti-BCMA antigen binding protein, a proteasome inhibitor, and, optionally, an anti-inflammatory compound.

Also provided is use of a combination in the manufacture of a medicament for use in the treatment of cancer, wherein the combination comprises an anti-BCMA antigen binding protein, a proteasome inhibitor, and, optionally, an anti-inflammatory compound.

Provided herein is a kit for use in the treatment of cancer comprising:
 (i) an anti-BCMA antigen binding protein;
 (ii) instructions for use in the treatment of cancer when combined with a proteasome inhibitor and, optionally, an anti-inflammatory compound.

DETAILED DESCRIPTION OF THE INVENTION

The disclosure relates to methods of treating cancer in a subject. In particular, the present invention relates to a combination of an anti-BCMA antigen binding protein and a proteasome inhibitor for treating cancer. Combinations may further include an anti-inflammatory compound such as dexamethasone. Without being bound by theory, it is believed that the novel combination(s) described herein result in reduced toxicities due to non-overlapping mechanisms of action.

Combinations and Pharmaceutical Compositions

The term "combination" described herein refers to at least two therapeutic agents. As used herein the term "therapeutic agent" is understood to mean a substance that produces a desired effect in a tissue, system, animal, mammal, human, or other subject. In one embodiment the combination is an anti-BCMA antigen binding protein, suitably an anti-BCMA antibody, and at least one additional therapeutic agent. In one embodiment, the combination is an anti-BCMA antigen binding protein and a proteasome inhibitor. In another embodiment, the combination is an anti-BCMA antigen binding protein, a proteasome inhibitor, and an anti-inflammatory compound. The combinations described herein can be effective in treating cancer.

In one embodiment, the combination can contain an additional therapeutic agent, such as, for example, an additional cancer therapeutic agent. In embodiment the additional cancer therapeutic is an immunomodulatory imide drug (IMiD) such as thalidomide, lenalidomide, pomalidomide, apremilast, or other thalidomide analogs.

The administration of the combinations of the invention may be advantageous over the individual therapeutic agents in that the combinations may provide one or more of the following improved properties when compared to the individual administration of a single therapeutic agent alone: i) a greater anticancer effect than the most active single agent, ii) synergistic or highly synergistic anticancer activity, iii) a dosing protocol that provides enhanced anticancer activity with reduced side effect profile, iv) a reduction in the toxic effect profile, v) an increase in the therapeutic window, or vi) an increase in the bioavailability of one or both of the therapeutic agents.

The combinations described herein can be in the form of a pharmaceutical composition. A "pharmaceutical composition" contains a combination described herein, and one or more pharmaceutically acceptable carriers, diluents, or excipients. The carrier(s), diluent(s) or excipient(s) must be acceptable in the sense of being compatible with the other ingredients of the formulation, capable of pharmaceutical formulation, and not deleterious to the recipient thereof.

In one embodiment, each therapeutic agent in a combination is individually formulated into its own pharmaceutical composition and each of the pharmaceutical compositions are administered to treat cancer. In this embodiment, each of the pharmaceutical compositions may have the same or different carriers, diluents or excipients. For example, in one embodiment, a first pharmaceutical composition contains an anti-BCMA antigen binding protein, a second pharmaceutical composition contains a proteasome inhibitor, and the first and second pharmaceutical compositions are both administered to treat cancer. In another embodiment, a first pharmaceutical composition contains an anti-BCMA antigen binding protein, a second pharmaceutical composition contains a proteasome inhibitor, a third pharmaceutical composition contains an anti-inflammatory compound, and the first, second, and third pharmaceutical compositions are each administered to treat cancer.

In one embodiment, each therapeutic agent in a combination is formulated together into a single pharmaceutical composition and administered to treat cancer. For example, in one embodiment, a single pharmaceutical composition contains both an anti-BCMA antigen binding protein and a proteasome inhibitor and is administered as a single pharmaceutical composition to treat cancer. In another embodiment, a single pharmaceutical composition contains an anti-BCMA antigen binding protein, a proteasome inhibitor, and an anti-inflammatory compound and is administered as a single pharmaceutical composition to treat cancer.

It is to be understood that references herein to the proteasome inhibitors and anti-inflammatory compounds mean the proteasome inhibitors and anti-inflammatory compound as the free base, or as a salt, for example a pharmaceutically acceptable salt. Pharmaceutically acceptable salts include acid addition salts. For a review on suitable salts see Berge et al., J. Pharm. Sci., 66:1-19 (1977).

The invention includes within its scope all possible stoichiometric and non-stoichiometric forms of the salts of the proteasome inhibitor and anti-inflammatory compound.

It will be appreciated that many organic compounds can form complexes with solvents in which they are reacted or from which they are precipitated or crystallized. These complexes are known as "solvates". For example, a complex with water is known as a "hydrate". Solvents with high boiling points and/or solvents with a high propensity to form hydrogen bonds such as water, ethanol, iso-propyl alcohol, and N-methyl pyrrolidinone may be used to form solvates. Methods for the identification of solvated include, but are not limited to, NMR and microanalysis. Solvates of the proteasome inhibitor and anti-inflammatory compounds are within the scope of the invention. As used herein, the term solvate encompasses solvates of both a free base proteasome inhibitor and anti-inflammatory compound as well as any salt thereof.

Certain proteasome inhibitors and anti-inflammatory compounds of the invention may contain chiral atoms and hence may exist in one or more stereoisomeric forms. The present invention encompasses all of the stereoisomers of the proteasome inhibitor and anti-inflammatory compounds of the invention, including optical isomers, whether as individual stereoisomers or as mixtures thereof including racemic modifications and mixtures. Any stereoisomer may contain less than 10% by weight, for example less than 5% by weight, or less than 0.5% by weight, of any other stereoisomer. For example, any optical isomer may contain less than 10% by weight, for example less than 5% by weight, or less than 0.5% by weight, of its antipode.

Certain proteasome inhibitors and anti-inflammatory compounds of the invention may exist in tautomeric forms. It will be understood that the present invention encompasses all of the tautomers of the proteasome inhibitors and anti-inflammatory compounds of the invention whether as individual tautomers or as mixtures thereof.

The proteasome inhibitor and anti-inflammatory compound of the invention may be in crystalline or amorphous form. Furthermore, some of the crystalline forms of the proteasome inhibitor and anti-inflammatory compound of the invention may exist as polymorphs, all of which are included within the scope of the present invention. The most thermodynamically stable polymorphic form or forms of the proteasome inhibitor and anti-inflammatory compound of the invention are of particular interest.

Polymorphic forms of the proteasome inhibitor and anti-inflammatory compound of the invention may be characterized and differentiated using a number of conventional analytical techniques, including, but not limited to, X-ray powder diffraction (XRPD), infrared spectroscopy (IR), Raman spectroscopy, differential scanning calorimetry (DSC), thermogravimetric analysis (TGA) and solid-state nuclear magnetic resonance (ssNMR).

The present invention also includes all suitable isotopic variations of the proteasome inhibitor and anti-inflammatory compound or a pharmaceutically acceptable salt thereof. An isotopic variation of the proteasome inhibitors and anti-inflammatory compounds, or a pharmaceutically acceptable salt thereof, is defined as one in which at least one atom is replaced by an atom having the same atomic number but an atomic mass different from the atomic mass usually found in nature. Examples of isotopes that can be incorporated into proteasome inhibitors and anti-inflammatory compounds of the invention include isotopes of hydrogen, carbon, nitrogen, oxygen, fluorine and chlorine such as $^{2}H$, $^{3}H$, $^{13}C$, $^{14}C$, $^{15}N$, $^{17}O$, $^{18}O$, $^{18}F$ and $^{36}Cl$, respectively. Certain isotopic variations of the proteasome inhibitor and anti-inflammatory compound or a salt or solvate thereof, for example, those in which a radioactive isotope such as $^{3}H$ or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and detectability. Further, substitution with isotopes such as deuterium, i.e., $^{2}H$, may afford certain therapeutic advantages resulting from greater metabolic stability, for example, increased in vivo half-life or reduced dosage requirements and hence may be preferred in some circumstances. Isotopic variations of the proteasome inhibitors, or a pharmaceutically salt thereof, can generally be prepared by conventional procedures.

It will be appreciated from the foregoing that included within the scope of the invention are solvates, hydrates, isomers and polymorphic forms of the proteasome inhibitor and anti-inflammatory compound and salts and solvates thereof.

It will be appreciated by those skilled in the art that certain derivatives of the proteasome inhibitor and anti-inflammatory compound, whilst not necessarily possessing pharmacological activity as such, may be administered and thereafter metabolised in the body to form proteasome inhibitors and anti-inflammatory compounds that are pharmacologically active. Such derivatives are herein referred to as "prodrugs". Accordingly, the proteasome inhibitor and anti-inflammatory compound described herein may exist in the form of a prodrug. Examples of suitable derivatives are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1.

Anti-BCMA Antigen Binding Proteins

The anti-BCMA antigen binding proteins in the combinations described herein are useful in the treatment or prevention of cancers. Any of the anti-BCMA antigen binding proteins disclosed herein may be used in combination with a proteasome inhibitor or in combination with a proteasome inhibitor and an anti-inflammatory compound for treating cancer. The anti-BCMA antigen binding proteins described herein may bind to human BCMA having, including, for example, human BCMA containing the amino acid sequence of GenBank Accession Number Q02223.2, or genes encoding human BCMA having at least 90 percent homology or at least 90 percent identity thereto.

The term "antigen binding protein" as used herein refers to antibodies, antibody fragments and other protein constructs which are capable of binding to human BCMA. The antigen binding proteins of the present invention may comprise heavy chain variable regions and light chain variable regions of the invention which may be formatted into the structure of a natural antibody or functional fragment or equivalent thereof. An antigen binding protein of the invention may therefore comprise the VH regions of the invention formatted into a full length antibody, a (Fab')2 fragment, a Fab fragment, or equivalent thereof (such as scFV, bi- tri- or tetra-bodies, Tandabs etc.), when paired with an appropriate light chain. The antibody may be an IgG1, IgG2, IgG3, or IgG4; or IgM; IgA, IgE or IgD or a modified variant thereof. The constant domain of the antibody heavy chain may be selected accordingly. The light chain constant domain may be a kappa or lambda constant domain. Furthermore, the antigen binding protein may comprise modifications of all classes e.g. IgG dimers, Fc mutants that no longer bind Fc receptors or mediate C1q binding. The antigen binding protein may also be a chimeric antibody of the type described in WO86/01533 which comprises an antigen binding region and a non-immunoglobulin region.

In another aspect the antigen binding protein is selected from the group consisting of a dAb, Fab, Fab', F(ab')2, Fv, diabody, triabody, tetrabody, miniantibody, and a minibody. In one aspect of the present invention the antigen binding protein is a humanised or chimaeric antibody, in a further aspect the antibody is humanised. In one aspect the antibody is a monoclonal antibody.

Chimeric antigen receptors (CARs) have been developed as artificial T cell receptors to generate novel specificities in T cells without the need to bind to MHC-antigenic peptide complexes. These synthetic receptors contain a target binding domain that is associated with one or more signalling domains via a flexible linker in a single fusion molecule. The target binding domain is used to target the T cell to specific targets on the surface of pathologic cells and the signalling domains contain molecular machinery for T cell activation and proliferation. The flexible linker which passes through the T cell membrane (i.e. forming a transmembrane domain) allows for cell membrane display of the target binding domain of the CAR. CARs have successfully allowed T cells to be redirected against antigens expressed at the surface of tumour cells from various malignancies including lymphomas and solid tumours (Jena et al. (2010) Blood, 116(7): 1035-44).

The development of CARs has comprised three generations so far. The first generation CARs comprised target binding domains attached to a signalling domain derived from the cytoplasmic region of the CD3zeta or the Fc receptor gamma chains. First generation CARs were shown to successfully redirect T cells to the selected target, however, they failed to provide prolonged expansion and anti-tumor activity in vivo. The second and third generation CARs have focused on enhancing modified T cell survival and increasing proliferation by including co-stimulatory molecules, such as CD28, OX-40 (CD134) and 4-1BB (CD137).

T cells bearing CARs could be used to eliminate pathologic cells in a disease setting. One clinical aim would be to transform patient cells with recombinant DNA containing an expression construct for the CAR via a vector (e.g. a lentiviral vector) following aphaeresis and T cell isolation. Following expansion of the T cells they are re-introduced into the patient with the aim of targeting and killing the pathologic target cells.

In one aspect of the invention the anti-BCMA antigen binding protein is a chimeric antigen receptor. In a further aspect the CAR comprises a binding domain, a transmembrane domain and an intracellular effector domain.

In one aspect, the transmembrane domain can be derived either from a natural or from a synthetic source. In one aspect, the transmembrane domain can be derived from any membrane-bound or transmembrane protein. Alternatively the transmembrane domain can be synthetic and can comprise predominantly hydrophobic residues such as leucine and valine. For example, the transmembrane domain can be the transmembrane domain of CD proteins, such as CD4, CD8, CD3 or CD28, a subunit of the T cell receptor, such as $\alpha$, $\beta$, $\gamma$ or $\delta$, a subunit of the IL-2 receptor ($\alpha$ chain), a submit of the Low-Affinity Nerve Growth Factor Receptor (LNGFR or p75) ($\beta$ chain or $\gamma$ chain), or a subunit chain of Fc receptors.

In one aspect, the transmembrane domain comprises the transmembrane domain of CD4, CD8 or CD28. In a further aspect, the transmembrane domain comprises the transmembrane domain of CD4 or CD8 (e.g. the CD8 alpha chain, as described in NCBI Reference Sequence: NP_001139345.1, incorporated herein by reference). In a yet further aspect, the transmembrane domain comprises the transmembrane domain of CD4.

The intracellular effector domain or "signalling domain" is responsible for intracellular signalling following the binding of the target binding domain to the target. The intracellular effector domain is responsible for the activation of at least one of the normal effector functions of the immune cell in which the CAR is expressed. For example, the effector function of a T cell can be a cytolytic activity or helper activity including the secretion of cytokines. Preferred examples of the effector domain for use in a CAR scaffold can be the cytoplasmic sequences of the natural T cell receptor and co-receptors that act in concert to initiate signal transduction following antigen binding, as well as any derivate or variant of these sequences and any synthetic sequence that has the same functional capability.

Effector domains can be separated into two classes: those that initiate antigen-dependent primary activation, and those that act in an antigen-independent manner to provide a secondary or costimulatory signal. Primary activation effector domains can comprise signalling motifs which are known as immunoreceptor tyrosine-based activation motifs (ITAMs). ITAMs are well defined signalling motifs, commonly found in the intracytoplasmic tail of a variety of receptors, and serve as binding sites for syk/zap70 class tyrosine kinases. Examples of ITAMs used in the invention can include, as non-limiting examples, those derived from CD3zeta, FcRgamma, FcRbeta, FcRepsilon, CD3gamma, CD3delta, CD3epsilon, CD5, CD22, CD79a, CD79b and CD66d. In one aspect, the intracellular effector domain comprises a CD3zeta signalling domain (also known as CD247). Natural TCRs contain a CD3zeta signalling molecule, therefore the use of this effector domain is closest to the TCR construct which occurs in nature.

In one aspect of the invention the intracellular signalling domain is a CD3 zeta effector domain. Effector domains may also provide a secondary or costimulatory signal. T cells additionally comprise costimulatory molecules which bind to cognate costimulatory ligands on antigen presenting cells in order to enhance the T cell response, for example by increasing proliferation activation, differentiation and the like. Therefore, in one aspect, the intracellular effector domain additionally comprises a costimulatory domain. In a further aspect, the costimulatory domain comprises the intracellular domain of a costimulatory molecule, selected from CD28, CD27, 4-1BB (CD137), OX40 (CD134), ICOS (CD278), CD30, CD40, PD-1 (CD279), CD2, CD7, NKG2C (CD94), B7-H3 (CD276) or any combination thereof. In a yet further aspect, the costimulatory domain comprises the intracellular domain of a costimulatory molecule, selected from CD28, CD27, 4-1BB, OX40, ICOS or any combination thereof.

Exemplary anti-BCMA antigen binding proteins and methods of making the same are disclosed in International Publication No. WO2012/163805 which is incorporated by reference herein in its entirety. Additional exemplary anti-BCMA antigen binding proteins include those described in WO2016/014789, WO2016/090320, WO2016/090327, WO2016/020332, WO2016/079177, WO2014/122143, WO2014/122144, WO2017/021450, WO2016/014565, WO2014/068079, WO2015/166649, WO2015/158671, WO2015/052536, WO2014/140248, WO2013/072415, WO2013/072406, WO2014/089335, US2017/165373, WO2013/154760, and WO2017/051068, each of which is incorporated by reference herein in its entirety.

In one embodiment, the anti-BCMA antigen binding protein has enhanced antibody dependent cell mediated cytotoxic activity (ADCC) effector function. The term "Effector Function" as used herein is meant to refer to one or more of Antibody dependent cell mediated cytotoxic activity (ADCC), Complement-dependent cytotoxic activity (CDC) mediated responses, Fc-mediated phagocytosis and antibody recycling via the FcRn receptor. For IgG antibodies, effector functionalities including ADCC and ADCP are mediated by the interaction of the heavy chain constant region with a family of Fcgamma receptors present on the surface of immune cells. In humans these include FcgammaRI (CD64), FcgammaRII (CD32) and FcgammaRIII (CD16). Interaction between the antigen binding protein bound to antigen and the formation of the Fc/Fcgamma complex induces a range of effects including cytotoxicity, immune cell activation, phagocytosis and release of inflammatory cytokines.

In another embodiment, the anti-BCMA antigen binding proteins described herein inhibit the binding of BAFF and/or APRIL to the BCMA receptor. In another embodiment, the anti-BCMA antigen binding proteins described herein are capable of binding to FcgammaRIIIA or is capable of FcgammaRIIIA mediated effector function.

In one embodiment, the anti-BCMA antigen binding protein is an antibody comprising a heavy chain variable region CDR1 ("CDRH1") comprising an amino acid sequence with at least 90%, 91%, 92%, 93%, 94%, 95%, 96%, 97%, 98%, 99% or 100% sequence identity to the amino acid sequence set forth in SEQ ID NO:1. In one embodiment, the heavy chain variable region CDR1 ("CDRH1") comprises an amino acid sequence with one amino acid variation (variant) to the amino acid sequence set forth in SEQ ID NO:1.

In one embodiment, the anti-BCMA antigen binding protein is an antibody comprising a heavy chain variable region CDR2 ("CDRH2") comprising an amino acid sequence with at least 90%, 91%, 92%, 93%, 94%, 95%, 96%, 97%, 98%, 99% or 100% sequence identity to the amino acid sequence set forth in SEQ ID NO:2. In one embodiment, the heavy chain variable region CDR2 ("CDRH2") comprises an amino acid sequence with one amino acid variation (variant) to the amino acid sequence set forth in SEQ ID NO:2.

In one embodiment, the anti-BCMA antigen binding protein is an antibody comprising a heavy chain variable region CDR3 ("CDRH3") comprising an amino acid sequence with at least 90%, 91%, 92%, 93%, 94%, 95%, 96%, 97%, 98%, 99% or 100% sequence identity to the amino acid sequence set forth in SEQ ID NO:3. In one embodiment, the heavy chain variable region CDR3 ("CDRH3") comprises an amino acid sequence with one amino acid variation (variant) to the amino acid sequence set forth in SEQ ID NO:3.

In one embodiment, the anti-BCMA antigen binding protein is an antibody comprising a light chain variable region CDR1 ("CDRL1") comprising an amino acid sequence with at least 90%, 91%, 92%, 93%, 94%, 95%, 96%, 97%, 98%, 99% or 100% sequence identity to the amino acid sequence set forth in SEQ ID NO:4. In one embodiment, the light chain variable region CDL1 ("CDR1") comprises an amino acid sequence with one amino acid variation (variant) to the amino acid sequence set forth in SEQ ID NO:4.

In one embodiment, the anti-BCMA antigen binding protein is an antibody comprising a light chain variable region CDR2 ("CDRL2") comprising an amino acid sequence with at least 90%, 91%, 92%, 93%, 94%, 95%, 96%, 97%, 98%, 99% or 100% sequence identity to the amino acid sequence set forth in SEQ ID NO:5. In one embodiment, the light chain variable region CDL2 ("CDR2") comprises an amino acid sequence with one amino acid variation (variant) to the amino acid sequence set forth in SEQ ID NO:5.

In one embodiment, the anti-BCMA antigen binding protein is an antibody comprising a light chain variable region CDR3 ("CDRL3") comprising an amino acid sequence with at least 90%, 91%, 92%, 93%, 94%, 95%, 96%, 97%, 98%, 99% or 100% sequence identity to the amino acid sequence set forth in SEQ ID NO:6. In one embodiment, the light chain variable region CDL3 ("CDR3") comprises an amino acid sequence with one amino acid variation (variant) to the amino acid sequence set forth in SEQ ID NO:6.

In one embodiment, the anti-BCMA antigen binding protein is an antibody comprising a CDRH1 comprising an amino acid sequence with at least 90%, 91%, 92%, 93%, 94%, 95%, 96%, 97%, 98%, 99% or 100% sequence identity to the amino acid sequence set forth in SEQ ID NO:1; CDRH2 comprising an amino acid sequence with at least 90%, 91%, 92%, 93%, 94%, 95%, 96%, 97%, 98%, 99% or 100% sequence identity to the amino acid sequence set forth in SEQ ID NO:2; CDRH3 comprising an amino acid sequence with at least 90%, 91%, 92%, 93%, 94%, 95%, 96%, 97%, 98%, 99% or 100% sequence identity to the amino acid sequence set forth in SEQ ID NO:3; CDRL1 comprising an amino acid sequence with at least 90%, 91%, 92%, 93%, 94%, 95%, 96%, 97%, 98%, 99% or 100% sequence identity to the amino acid sequence set forth in SEQ ID NO:4; CDRL2 comprising an amino acid sequence with at least 90%, 91%, 92%, 93%, 94%, 95%, 96%, 97%, 98%, 99% or 100% sequence identity to the amino acid sequence set forth in SEQ ID NO:5; and/or CDRL3 comprising an amino acid sequence with at least 90%, 91%, 92%, 93%, 94%, 95%, 96%, 97%, 98%, 99% or 100% sequence identity to the amino acid sequence set forth in SEQ ID NO:6.

In one embodiment, the anti-BCMA antigen binding protein is an antibody comprising a heavy chain variable region ("VH") comprising an amino acid sequence with at least 90%, 91%, 92%, 93%, 94%, 95%, 96%, 97%, 98%, 99% or 100% sequence identity to the amino acid sequence set forth in SEQ ID NO:7.

In one embodiment, the anti-BCMA antigen binding protein is an antibody comprising a light chain variable region ("VL") comprising an amino acid sequence with at least 90%, 91%, 92%, 93%, 94%, 95%, 96%, 97%, 98%, 99% or 100% sequence identity to the amino acid sequence set forth in SEQ ID NO:8.

In one embodiment, the anti-BCMA antigen binding protein is an antibody comprising a VH comprising an amino acid sequence with at least 90%, 91%, 92%, 93%, 94%, 95%, 96%, 97%, 98%, 99% or 100% sequence identity to the amino acid sequence set forth in SEQ ID NO:7; and a VL comprising an amino acid sequence with at least 90%, 91%, 92%, 93%, 94%, 95%, 96%, 97%, 98%, 99% or 100% sequence identity to the amino acid sequence set forth in SEQ ID NO:8.

In one embodiment, the anti-BCMA antigen binding protein is an antibody comprising a heavy chain region ("HC") comprising an amino acid sequence with at least 90%, 91%, 92%, 93%, 94%, 95%, 96%, 97%, 98%, 99% or 100% sequence identity to the amino acid sequence set forth in SEQ ID NO:9.

In one embodiment, the anti-BCMA antigen binding protein is an antibody comprising a light chain region ("LC") comprising an amino acid sequence with at least 90%, 91%, 92%, 93%, 94%, 95%, 96%, 97%, 98%, 99% or 100% sequence identity to the amino acid sequence set forth in SEQ ID NO:10.

In one embodiment, the anti-BCMA antigen binding protein is an antibody comprising a HC comprising an amino acid sequence with at least 90%, 91%, 92%, 93%, 94%, 95%, 96%, 97%, 98%, 99% or 100% sequence identity to the amino acid sequence set forth in SEQ ID NO:9; and a LC comprising an amino acid sequence with at least 90%, 91%, 92%, 93%, 94%, 95%, 96%, 97%, 98%, 99% or 100% sequence identity to the amino acid sequence set forth in SEQ ID NO:10.

In one embodiment, the anti-BCMA antigen binding protein is an immunoconjugate comprising an antigen binding protein according to the invention as herein described including, but not limited to, an antibody conjugated to one or more cytotoxic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope (i.e., a radioconjugate). In a further embodiment the anti-BCMA antigen binding protein is conjugated to a toxin such as an auristatin, e.g., monomethyl auristatin E (MMAE) or monomethyl auristatin F (MMAF).

In one embodiment, the anti-BCMA antigen binding protein is an immunoconjugate having the following general structure:

ABP-((Linker)$_n$-Ctx)$_m$ wherein
ABP is an antigen binding protein
Linker is either absent or any a cleavable or non-cleavable linker
Ctx is any cytotoxic agent described herein
n is 0, 1, 2, or 3 and
m is 1, 2, 3, 4, 5, 6, 7, 8, 9 or 10.

Exemplary linkers include 6-maleimidocaproyl (MC), maleimidopropanoyl (MP), valine-citrulline (val-cit), alanine-phenylalanine (ala-phe), p-aminobenzyloxycarbonyl (PAB), N-Succinimidyl 4-(2-pyridylthio)pentanoate (SPP), N-succinimidyl 4-(N-maleimidomethyl)cyclohexane-1 carboxylate (SMCC), and N-Succinimidyl (4-iodo-acetyl) aminobenzoate (SIAB).

In one embodiment, the anti-BCMA antigen binding protein is an immunoconjugate containing a monoclonal antibody linked to MMAE or MMAF. In another embodiment, the anti-BCMA antigen binding protein is an immunoconjugate containing a monoclonal antibody linked to MMAE or MMAF by an MC linker as depicted in the following structures:

their weight, for example suitable doses may be in the range of about 0.1 to about 20 mg/kg, for example about 1 to about 20 mg/kg, for example about 10 to about 20 mg/kg or for example about 1 to about 15 mg/kg, for example about 10 to about 15 mg/kg.

In one embodiment, the therapeutically effective dose of the anti-BCMA antigen binding protein is in the range of about 0.03 mg/kg to about 4.6 mg/kg. In yet another embodiment, the therapeutically effective dose of the anti-BCMA antigen binding protein is 0.03 mg/kg, 0.06 mg/kg, 0.12 mg/kg, 0.24 mg/kg, 0.48 mg/kg, 0.96 mg/kg, 1.92 mg/kg, 3.4 mg/kg, or 4.6 mg/kg. In yet another embodiment, the therapeutically effective dose of the anti-BCMA antigen binding protein is 1.9 mg/kg, 2.5 mg/kg or 3.4 mg/kg.

Proteasome Inhibitors

The term "proteasome inhibitor" as used herein refers to a class of drugs that block the action of proteasomes, complexes of enzymes found in cells that normally regulates the removal of defective proteins. Without being bound by theory, it is believed that proteasome inhibition may prevent degradation of pro-apoptotic factors such as the p53 protein, permitting activation of programmed cell death in neoplastic cells dependent upon suppression of pro-apoptotic pathways, causing defective proteins to build up and die. Proteasome inhibitors are useful in the treatment of cancers as

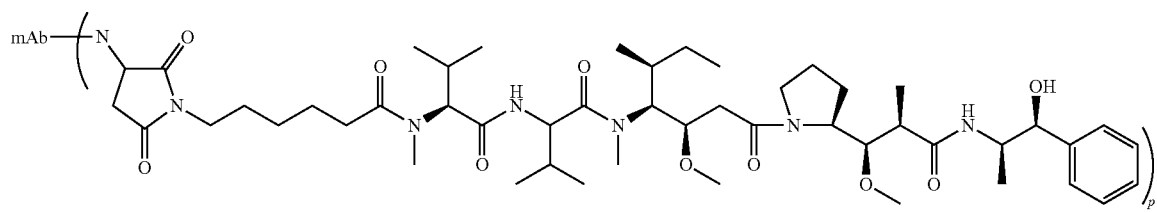

L-MC-MMAE

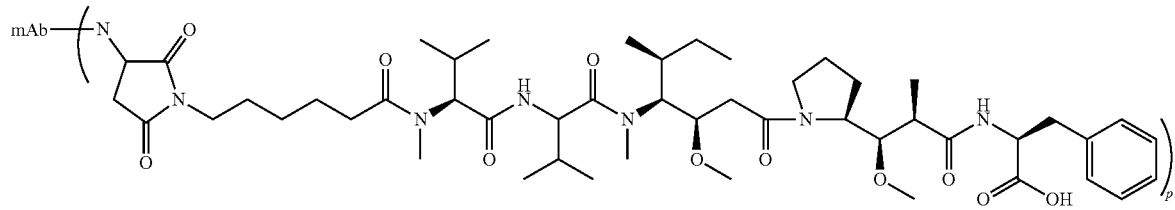

L-MC-MMAF

The appropriate therapeutically effective dose of the anti-BCMA antigen binding protein will be determined readily by those of skill in the art. As used herein, the term "effective dose" means that dose of a drug or pharmaceutical agent that will elicit the biological or medical response of a tissue, system, animal or human that is being sought, for instance, by a researcher or clinician. Furthermore, the term "therapeutically effective dose" means any dose which, as compared to a corresponding subject who has not received such dose, results in improved treatment, healing, prevention, or amelioration of a disease, disorder, or side effect, or a decrease in the rate of advancement of a disease or disorder. The term also includes within its scope doses effective to enhance normal physiological function.

Suitable doses of the anti-BCMA antigen binding proteins described herein may be calculated for patients according to it is believed that cancer cells are more sensitive than normal cells to this proteasome inhibitor effect.

Various proteasome inhibitors are known to those skilled in the art, including, for example, bortezomib, carfilzomib, ixazomib, oprozomib, and analogs thereof The term "analog" as used herein is a compound having a structure similar to that of another one, but differing from it in respect of a certain component, e.g., the analog can differ in one or more atoms, functional groups, or substructures, which are replaced with other atoms, groups, or substructures. Such differences in structure can be imaged, at least theoretically, from the other compound, by one skilled in the art.

In one embodiment, the proteasome inhibitor includes bortezomib or analogs thereof. Bortezomib is registered under the trade name Velcade® (Millennium Pharmaceuticals) and has the following chemical structure:

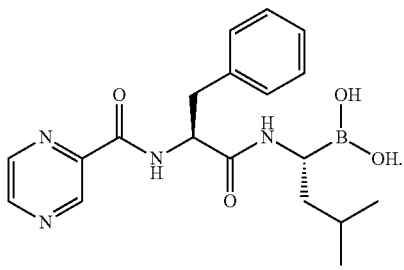 [SMILES: CC(C)C[C@H](NC(=O)[C@H](Cc1ccccc1)NC(=O)c1cnccn1)B(O)O]

Bortezomib and analogs thereof, and methods of making the same, are known to those skilled in the art, for example, those described in U.S. Pat. Nos. 5,780,454; 6,713,446; and 6,958,319, the disclosures of which are incorporated herein in their entireties.

In one embodiment, the proteasome inhibitor includes carfilzomib or analogs thereof. Carfilzomib is registered under the trade name Kyprolis® (Onyx Pharmaceuticals) and has the following chemical structure:

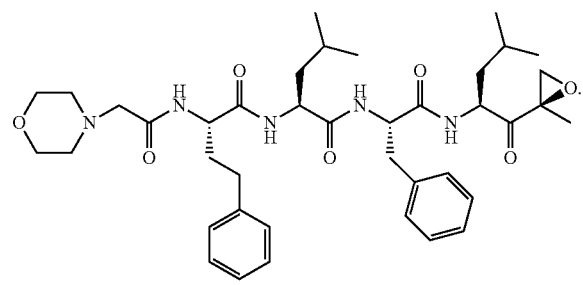 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

Carfilzomib and analogs thereof, and methods of making the same, are known to those skilled in the art, for example, those described in U.S. Pat. Nos. 7,232,818; 7,417,042; 7,737,112; 8,207,125; 8,207,126; 8,207,297; and 9,493,582 the disclosures of which are incorporated herein in their entireties.

In one embodiment, the proteasome inhibitor includes ixazomib, or analogs thereof. Ixazomib is registered under the trade name Ninlaro® (Millennium Pharmaceuticals) and has the following chemical structure:

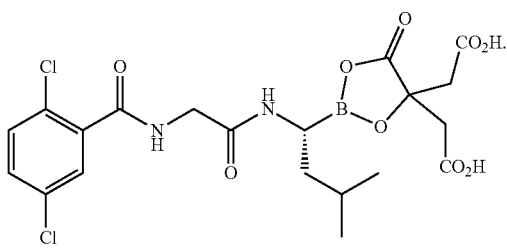 [SMILES: CC(C)C[C@H](NC(=O)CNC(=O)c1cc(Cl)ccc1Cl)B1OC(=O)C(CC(=O)O)(CC(=O)O)O1]

Ixazomib and analogs thereof, and methods of making the same, are known to those skilled in the art, for example, those described in U.S. Pat. Nos. 7,442,830; 7,687,662; 8,003,819; 8,530,694; 8,546,608; and 8,859,504, the disclosures of which are incorporated herein in their entireties.

In one embodiment, the proteasome inhibitor includes oprozomib, or analogs thereof. Oprozomib (Onyx Pharmaceuticals—ONX 0912 and PR-047) has the following chemical structure:

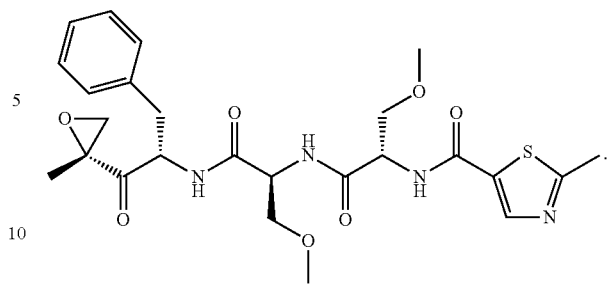

Oprozomib and analogs thereof, and methods of making the same, are known to those skilled in the art, for example, those described in WO2007/056464; WO2011/060179; WO2010/108172; and WO2014/066681, the disclosures of which are incorporated herein in their entireties.

The appropriate therapeutically effective dose of the proteasome inhibitor will be determined readily by those of skill in the art. Suitable doses of the proteasome inhibitor described herein may be calculated for patients according to their weight. The therapeutically effective dose will generally be between about 1 and 2000 mg, 5 and 2000 mg, 10 and 2000 mg and suitably between about 30 and 1500 mg. Other ranges may be used, including, for example, 50-500 mg, 50-300 mg, 50-100 mg, 100-200 mg, 5-100 mg, 5-50 mg. The therapeutically effective dose as employed for acute or chronic human treatment will range from 0.01 to 250 mg/kg body weight, suitably 0.1-5 mg/kg body weight, suitably 0.1-10 mg/kg body weight, suitably 2-100 mg/kg body weight, or suitably 5-60 mg/kg body weight, which may be administered, for example in one to four daily doses, depending on the route of administration and the condition of the subject.

In one embodiment, the proteasome inhibitor is bortezomib and the therapeutically effective dose is in the range of about 0.5 mg/m$^2$ to about 5 mg/m$^2$. In another embodiment, the proteasome inhibitor is bortezomib and the therapeutically effective dose is in the range of about 0.75 mg/m$^2$ to about 2.5 mg/m$^2$. In yet embodiment, the proteasome inhibitor is bortezomib and the therapeutically effective dose is 1.3 mg/m$^2$.

In one embodiment, the proteasome inhibitor is carfilzomib and the therapeutically effective dose is in the range of about 5 mg/m$^2$ to about 100 mg/m$^2$. In another embodiment, the proteasome inhibitor is carfilzomib and the therapeutically effective dose is in the range of about 10 mg/m$^2$ to about 60 mg/m$^2$. In yet embodiment, the proteasome inhibitor is carfilzomib and the therapeutically effective dose is 15 mg/m$^2$, 20 mg/m$^2$, 27 mg/m$^2$, 36 mg/m$^2$, 45 mg/m$^2$, or 56 mg/m$^2$.

In one embodiment, the proteasome inhibitor is ixazomib and the therapeutically effective dose is in the range of about 0.5 mg to about 10 mg. In another embodiment, the proteasome inhibitor is ixazomib and the therapeutically effective dose is in the range of about 1 mg to about 5 mg. In yet embodiment, the proteasome inhibitor is ixazomib and the therapeutically effective dose is 2.3 mg, 3 mg, or 4 mg.

Anti-Inflammatory Compound

Anti-inflammatory compounds, such as dexamethasone, are compounds that reduce inflammation or swelling in various parts of the body. Anti-inflammatory compounds have been used to decrease swelling (edema), associated with tumors of the spine and brain, and to treat eye inflammation, as well as treatment for a variety of cancers, such as leukemia, lymphoma, and multiple myeloma. Various anti-inflammatory compounds, and methods of making, are known to those skilled in the art.

Anti-inflammatory compounds can include both steroidal and nonsteroidal compounds (NSAIDs).

In one embodiment, the anti-inflammatory compound is a steroid. Examples of steroids include, but are not limited to, cortisone, cortisol, corticosterone, hydrocortisone, hydrocortisol, prednisone, prednisolone, dexamethasone, beclomethasone, betamethasone, mometasone, mometasone furoate, budesonide, triamcinolone acetonide, and fluticasone. In one embodiment, the anti-inflammatory compound is an adrenal corticosteroid selected from dexamethasone, prednisone, prednisolone, methylprednisone, and methylprednisolone.

In another embodiment, the anti-inflammatory compound is dexamethasone. Dexamethasone has the following chemical structure and is registered under the trade name Decadron® (Merck & Co., Inc.):

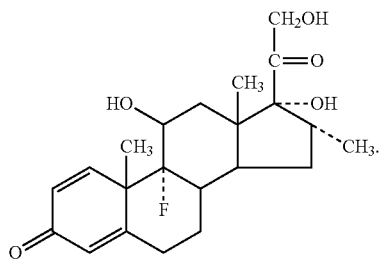

In another embodiment, the anti-inflammatory compound is an NSAID. Examples of NSAIDs which may be used in the invention include, but are not limited to, aspirin, acetominophen, ibuprofen, esculetin, phenidone, quercetin, ketoprofen, nordihydroguiaretic acid. (NDGA), sulindac, sulindac sulfone, sulindac sulfide, indomethacin, NS-398 (a cyclooxygenase-2 inhibitor), cyclooxygenase-1 inhibitors, methylheptyl imidazole, furegrelate sodium, SKF525AHCL, thromboxane inhibitors, toradol, ecasa, salsalate, diflunisal, mefenamic acid, naproxen, naproxen sodium, floctafenine, meclofenamate, phenylbutazone, oxyphenbutazone, diclofenac, etodolac, fenoprofen, flufenamic acid, flurbiprofen, pirprofen, tolmetin, apazone, fenbufen, nabumetone, oxaprozin, piroxicam, salicylate, and tenoxicam. Preferred NSAIDs are sulindac, sulindac sulfone, sulindac sulfide, indomethacin, NS-398, methylheptyl imidazole, furegrelate sodium, and SKF525AHCL. Especially preferred NSAIDs are indomethacin and sulindac.

The appropriate therapeutically effective dose of the anti-inflammatory compound can be determined readily by those of skill in the art. Suitable doses of an anti-inflammatory compound described herein may be calculated for patients according to their weight. The therapeutically effective dose will generally be between about 1 and 2000 mg, 5 and 2000 mg, 10 and 2000 mg and suitably between about 30 and 1500 mg. Other ranges may be used, including, for example, 50-500 mg, 50-300 mg, 50-100 mg, 100-200 mg, 5-100 mg, 5-50 mg. The daily dose as employed for acute or chronic human treatment will range from 0.01 to 250 mg/kg body weight, suitably 0.1-5 mg/kg body weight, suitably 0.1-10 mg/kg body weight, suitably 2-100 mg/kg body weight, or suitably 5-60 mg/kg body weight, which may be administered in one to four daily doses, for example, depending on the route of administration and the condition of the subject.

In one embodiment, anti-inflammatory compound dexamethasone and the therapeutically effective dose is about 5 mg to about 100 mg. In another embodiment, the anti-inflammatory compound is dexamethasone and the therapeutically effective dose is 20 mg or 40 mg.

Methods of Treatment

Described herein are methods for treating cancer in a subject with the combinations described herein. As used herein, the terms "cancer," and "tumor" are used interchangeably and, in either the singular or plural form, refer to cells that have undergone a malignant transformation that makes them pathological to the host organism. Primary cancer cells can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as computed tomography (CT) scan, magnetic resonance imaging (MRI), X-ray, ultrasound or palpation on physical examination, and/or which is detectable because of the expression of one or more cancer-specific antigens in a sample obtainable from a patient. Tumors may be a hematopoietic (or hematologic or hematological or blood-related) cancer, for example, cancers derived from blood cells or immune cells, which may be referred to as "liquid tumors." Specific examples of clinical conditions based on hematologic tumors include leukemias such as chronic myelocytic leukemia, acute myelocytic leukemia, chronic lymphocytic leukemia and acute lymphocytic leukemia; plasma cell malignancies such as multiple myeloma, MGUS and Waldenstrom's macroglobulinemia; lymphomas such as non-Hodgkin's lymphoma, Hodgkin's lymphoma; and the like.

The cancer may be any in which an abnormal number of blast cells or unwanted cell proliferation is present or that is diagnosed as a hematological cancer, including both lymphoid and myeloid malignancies. Myeloid malignancies include, but are not limited to, acute myeloid (or myelocytic or myelogenous or myeloblastic) leukemia (undifferentiated or differentiated), acute promyeloid (or promyelocytic or promyelogenous or promyeloblastic) leukemia, acute myelomonocytic (or myelomonoblastic) leukemia, acute monocytic (or monoblastic) leukemia, erythroleukemia and megakaryocytic (or megakaryoblastic) leukemia. These leukemias may be referred together as acute myeloid (or myelocytic or myelogenous) leukemia (AML). Myeloid malignancies also include myeloproliferative disorders (MPD) which include, but are not limited to, chronic myelogenous (or myeloid) leukemia (CML), chronic myelomonocytic leukemia (CMML), essential thrombocythemia (or thrombocytosis), and polcythemia vera (PCV). Myeloid malignancies also include myelodysplasia (or myelodysplastic syndrome or MDS), which may be referred to as refractory anemia (RA), refractory anemia with excess blasts (RAEB), and refractory anemia with excess blasts in transformation (RAEBT); as well as myelofibrosis (MFS) with or without agnogenic myeloid metaplasia.

Hematopoietic cancers also include lymphoid malignancies, which may affect the lymph nodes, spleens, bone marrow, peripheral blood, and/or extranodal sites. Lymphoid cancers include B-cell malignancies, which include, but are not limited to, B-cell non-Hodgkin's lymphomas (B-NHLs). B-NHLs may be indolent (or low-grade), intermediate-grade (or aggressive) or high-grade (very aggressive). Indolent B-cell lymphomas include follicular lymphoma (FL); small lymphocytic lymphoma (SLL); marginal zone lymphoma (MZL) including nodal MZL, extranodal MZL, splenic MZL and splenic MZL with villous lymphocytes; lymphoplasmacytic lymphoma (LPL); and mucosa-associated-lymphoid tissue (MALT or extranodal marginal zone) lymphoma. Intermediate-grade B-NHLs include mantle cell lymphoma (MCL) with or without leukemic involvement, diffuse large cell lymphoma (DLBCL), follicular large cell (or grade 3 or grade 3B) lymphoma, and primary mediastinal lymphoma (PML). High-grade B-NHLs include Burkitt's lymphoma (BL), Burkitt-like lymphoma, small non-cleaved cell lymphoma (SNCCL) and lymphoblastic lymphoma. Other B-NHLs include immunoblastic lymphoma (or immunocytoma), primary effusion lymphoma, HIV associated (or AIDS related) lymphomas, and post-transplant lymphoproliferative disorder (PTLD) or lymphoma. B-cell malignancies also include, but are not limited to, chronic lymphocytic leukemia (CLL), prolymphocytic leukemia (PLL), Waldenstrom's macroglobulinemia (WM), hairy cell leukemia (HCL), large granular lymphocyte (LGL) leukemia, acute lymphoid (or lymphocytic or lymphoblastic) leukemia, and Castleman's disease. NHL may also include T-cell non-Hodgkin's lymphoma s(T-NHLs), which include, but are not limited to T-cell non-Hodgkin's lymphoma not otherwise specified (NOS), peripheral T-cell lymphoma (PTCL), anaplastic large cell lymphoma (ALCL), angioimmunoblastic lymphoid disorder (AILD), nasal natural killer (NK) cell/T-cell lymphoma, gamma/delta lymphoma, cutaneous T cell lymphoma, mycosis fungoides, and Sezary syndrome.

Hematopoietic cancers also include Hodgkin's lymphoma (or disease) including classical Hodgkin's lymphoma, nodular sclerosing Hodgkin's lymphoma, mixed cellularity Hodgkin's lymphoma, lymphocyte predominant (LP) Hodgkin's lymphoma, nodular LP Hodgkin's lymphoma, and lymphocyte depleted Hodgkin's lymphoma. Hematopoietic cancers also include plasma cell diseases or cancers such as multiple myeloma (MM) including smoldering MM, monoclonal gammopathy of undetermined (or unknown or unclear) significance (MGUS), plasmacytoma (bone, extramedullary), lymphoplasmacytic lymphoma (LPL), Waldenstroem's Macroglobulinemia, plasma cell leukemia, and primary amyloidosis (AL). Hematopoietic cancers may also include other cancers of additional hematopoietic cells, including polymorphonuclear leukocytes (or neutrophils), basophils, eosinophils, dendritic cells, platelets, erythrocytes and natural killer cells. Tissues which include hematopoietic cells referred herein to as "hematopoietic cell tissues" include bone marrow; peripheral blood; thymus; and peripheral lymphoid tissues, such as spleen, lymph nodes, lymphoid tissues associated with mucosa (such as the gut-associated lymphoid tissues), tonsils, Peyer's patches and appendix, and lymphoid tissues associated with other mucosa, for example, the bronchial linings.

The term "treating" and derivatives thereof as used herein, is meant to include therapeutic therapy. In reference to a particular condition, treating means: (1) to ameliorate the condition or one or more of the biological manifestations of the condition; (2) to interfere with (a) one or more points in the biological cascade that leads to or is responsible for the condition or (b) one or more of the biological manifestations of the condition; (3) to alleviate one or more of the symptoms, effects or side effects associated with the condition or one or more of the symptoms, effects or side effects associated with the condition or treatment thereof; (4) to slow the progression of the condition or one or more of the biological manifestations of the condition and/or (5) to cure said condition or one or more of the biological manifestations of the condition by eliminating or reducing to undetectable levels one or more of the biological manifestations of the condition for a period of time considered to be a state of remission for that manifestation without additional treatment over the period of remission. One skilled in the art will understand the duration of time considered to be remission for a particular disease or condition.

Prophylactic therapy is also contemplated. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof. Prophylactic therapy is appropriate, for example, when a subject is considered at high risk for developing cancer, such as when a subject has a strong family history of cancer or when a subject has been exposed to a carcinogen.

"Subject" is defined broadly to include any patient in need of treatment, for example, a patient in need of cancer treatment. A subject may include a mammal. In one embodiment, the subject is a human patient. The subject in need of cancer treatment may include patients from a variety of stages including newly diagnosed, relapsed, refractory, progressive disease, remission, and others. The subject in need of cancer treatment may also include patients who have undergone stem cell transplant or who are considered transplant ineligible.

Subjects may be pre-screened in order to be selected for treatment with the combinations described herein. In one embodiment, a sample from the subject is tested for expression of BCMA prior to treatment with the combinations described herein.

Subjects may have had at least one prior cancer treatment before being treated with the combinations of the present invention. In one embodiment, the subject has been treated with at least 1, at least 2, at least 3, at least 4, at least 5, at least 6, or at least 7 prior cancer treatments before being treated with the combinations of the present invention.

In another embodiment, the subject has newly diagnosed cancer and has had 0 prior treatments before being treated with the combinations of the present invention.

The individual therapeutic agents of the combination of the invention, and pharmaceutical compositions comprising such therapeutic agents may be administered together or separately. When administered separately, this may occur simultaneously or sequentially in any order (by the same or by different routes of administration). Such sequential administration may be close in time or remote in time. The dose of a therapeutic agents of the invention or pharmaceutically acceptable salt thereof and the further therapeutically active agent(s) and the relative timings of administration will be selected in order to achieve the desired combined therapeutic effect.

The therapeutic agents of the invention may be administered by any appropriate route. For some therapeutic agents, suitable routes include oral, rectal, nasal, topical (including buccal and sublingual), vaginal, and parenteral (including subcutaneous, intramuscular, intraveneous, intradermal, intrathecal, and epidural). It will be appreciated that the preferred route may vary with, for example, the condition of the recipient of the combination and the cancer to be treated. It will also be appreciated that each of the agents administered may be administered by the same or different routes and that the therapeutic agents may be formulated together or in separate pharmaceutical compositions.

In one embodiment, one or more therapeutic agents of a combination of the invention are administered intravenously. In another embodiment, one or more therapeutic agents of a combination of the invention are administered intratumorally. In another embodiment, one or more therapeutic agents of a combination of the invention are administered orally. In another embodiment, one or more therapeutic agents of a combination of the invention are administered systemically, e.g., intravenously, and one or more other therapeutic agents of a combination of the invention are administered intratumorally. In another embodiment, all of the therapeutic agents of a combination of the invention are administered systemically, e.g., intravenously. In an alternative embodiment, all of the therapeutic agents of the combination of the invention are administered intratumorally. In any of the embodiments, e.g., in this paragraph, the therapeutic agents of the invention are administered as one or more pharmaceutical compositions.

In one embodiment, the invention provides a method of treating cancer in a subject in need thereof by administering a therapeutically effective dose of a combination described herein.

In one embodiment, the invention provides a method of treating cancer in a subject in need thereof by administering a therapeutically effective dose of a combination comprising an anti-BCMA antigen binding protein and a proteasome inhibitor.

In one embodiment, the invention provides a method of treating cancer in a subject in need thereof by administering a therapeutically effective dose of a combination comprising an anti-BCMA antigen binding protein, a proteasome inhibitor, and an anti-inflammatory compound.

In one embodiment, the invention provides a method of treating cancer in a subject in need thereof by administering a therapeutically effective dose of a combination comprising an anti-BCMA antibody and a proteasome inhibitor, wherein the anti-BCMA antibody comprises a CDRH1 comprising an amino acid sequence with at least 90%, 91%, 92%, 93%, 94%, 95%, 96%, 97%, 98%, 99% or 100% sequence identity to the amino acid sequence set forth in SEQ ID NO:1; a CDRH2 comprising an amino acid sequence with at least 90%, 91%, 92%, 93%, 94%, 95%, 96%, 97%, 98%, 99% or 100% sequence identity to the amino acid sequence set forth in SEQ ID NO:2; a CDRH3 comprising an amino acid sequence with at least 90%, 91%, 92%, 93%, 94%, 95%, 96%, 97%, 98%, 99% or 100% sequence identity to the amino acid sequence set forth in SEQ ID NO:3; a CDRL1 comprising an amino acid sequence with at least 90%, 91%, 92%, 93%, 94%, 95%, 96%, 97%, 98%, 99% or 100% sequence identity to the amino acid sequence set forth in SEQ ID NO:4; a CDRL2 comprising an amino acid sequence with at least 90%, 91%, 92%, 93%, 94%, 95%, 96%, 97%, 98%, 99% or 100% sequence identity to the amino acid sequence set forth in SEQ ID NO:5; and/or a CDRL3 comprising an amino acid sequence with at least 90%, 91%, 92%, 93%, 94%, 95%, 96%, 97%, 98%, 99% or 100% sequence identity to the amino acid sequence set forth in SEQ ID NO:6.

In one embodiment, the invention provides a method of treating cancer in a subject in need thereof by administering a therapeutically effective dose of a combination comprising an anti-BCMA antibody and a proteasome inhibitor, wherein the anti-BCMA antibody comprises a VH comprising an amino acid sequence with at least 90%, 91%, 92%, 93%, 94%, 95%, 96%, 97%, 98%, 99% or 100% sequence identity to the amino acid sequence set forth in SEQ ID NO:7; and/or a VL comprising an amino acid sequence with at least 90%, 91%, 92%, 93%, 94%, 95%, 96%, 97%, 98%, 99% or 100% sequence identity to the amino acid sequence set forth in SEQ ID NO:8.

In one embodiment, the invention provides a method of treating cancer in a subject in need thereof by administering a therapeutically effective dose of a combination comprising an anti-BCMA antibody and a proteasome inhibitor, wherein the anti-BCMA antibody comprises a HC comprising an amino acid sequence with at least 90%, 91%, 92%, 93%, 94%, 95%, 96%, 97%, 98%, 99% or 100% sequence identity to the amino acid sequence set forth in SEQ ID NO:9; and/or a LC comprising an amino acid sequence with at least 90%, 91%, 92%, 93%, 94%, 95%, 96%, 97%, 98%, 99% or 100% sequence identity to the amino acid sequence set forth in SEQ ID NO:10.

In one embodiment, the invention provides a method of treating cancer in a subject in need thereof by administering a therapeutically effective dose of a combination comprising an anti-BCMA antibody, a proteasome inhibitor, and an anti-inflammatory compound, wherein the anti-BCMA antibody comprises a CDRH1 comprising an amino acid sequence with at least 90%, 91%, 92%, 93%, 94%, 95%, 96%, 97%, 98%, 99% or 100% sequence identity to the amino acid sequence set forth in SEQ ID NO:1; a CDRH2 comprising an amino acid sequence with at least 90%, 91%, 92%, 93%, 94%, 95%, 96%, 97%, 98%, 99% or 100% sequence identity to the amino acid sequence set forth in SEQ ID NO:2; a CDRH3 comprising an amino acid sequence with at least 90%, 91%, 92%, 93%, 94%, 95%, 96%, 97%, 98%, 99% or 100% sequence identity to the amino acid sequence set forth in SEQ ID NO:3; a CDRL1 comprising an amino acid sequence with at least 90%, 91%, 92%, 93%, 94%, 95%, 96%, 97%, 98%, 99% or 100% sequence identity to the amino acid sequence set forth in SEQ ID NO:4; a CDRL2 comprising an amino acid sequence with at least 90%, 91%, 92%, 93%, 94%, 95%, 96%, 97%, 98%, 99% or 100% sequence identity to the amino acid sequence set forth in SEQ ID NO:5; and/or a CDRL3 comprising an amino acid sequence with at least 90%, 91%, 92%, 93%, 94%, 95%, 96%, 97%, 98%, 99% or 100% sequence identity to the amino acid sequence set forth in SEQ ID NO:6.

In one embodiment, the invention provides a method of treating cancer in a subject in need thereof by administering a therapeutically effective dose of a combination comprising an anti-BCMA antibody, a proteasome inhibitor, and an anti-inflammatory compound, wherein the anti-BCMA antibody comprising an anti-BCMA antibody and a proteasome inhibitor, wherein the anti-BCMA antibody comprises a VH comprising an amino acid sequence with at least 90%, 91%, 92%, 93%, 94%, 95%, 96%, 97%, 98%, 99% or 100% sequence identity to the amino acid sequence set forth in SEQ ID NO:7; and/or a VL comprising an amino acid sequence with at least 90%, 91%, 92%, 93%, 94%, 95%, 96%, 97%, 98%, 99% or 100% sequence identity to the amino acid sequence set forth in SEQ ID NO:8.

In one embodiment, the invention provides a method of treating cancer in a subject in need thereof by administering a therapeutically effective dose of a combination comprising an anti-BCMA antibody, a proteasome inhibitor, and an anti-inflammatory compound, wherein the anti-BCMA antibody comprises a HC comprising an amino acid sequence with at least 90%, 91%, 92%, 93%, 94%, 95%, 96%, 97%, 98%, 99% or 100% sequence identity to the amino acid sequence set forth in SEQ ID NO:9; and/or a LC comprising an amino acid sequence with at least 90%, 91%, 92%, 93%, 94%, 95%, 96%, 97%, 98%, 99% or 100% sequence identity to the amino acid sequence set forth in SEQ ID NO:10.

In one embodiment, the invention provides a method of treating cancer in a subject in need thereof by administering a therapeutically effective dose of a combination comprising an anti-BCMA antigen binding protein and bortezomib.

In one embodiment, the invention provides a method of treating cancer in a subject in need thereof by administering a therapeutically effective dose of a combination comprising an anti-BCMA antigen binding protein, bortezomib, and an anti-inflammatory compound.

In one embodiment, the invention provides a method of treating multiple myeloma in a subject in need thereof by administering a therapeutically effective dose of a combination comprising an anti-BCMA antibody, bortezomib and dexamethasone. In another embodiment, the invention provides a method of treating multiple myeloma in a subject in need thereof by administering 1.9 mg/kg, 2.5 mg·kg, or 3.4 mg/kg of an anti-BCMA antibody, 1.3 mg/m$^2$ of bortezomib, and 20 mg or 40 mg of dexamethasone.

In one embodiment, the invention provides a method of treating cancer in a subject in need thereof by administering a therapeutically effective dose of a combination comprising an anti-BCMA antigen binding protein and carfilzomib.

In one embodiment, the invention provides a method of treating cancer in a subject in need thereof by administering a therapeutically effective dose of a combination comprising an anti-BCMA antigen binding protein, carfilzomib, and an anti-inflammatory compound.

In one embodiment, the invention provides a method of treating multiple myeloma in a subject in need thereof by administering a therapeutically effective dose of a combination comprising an anti-BCMA antibody, carfilzomib and dexamethasone. In another embodiment, the invention provides a method of treating multiple myeloma in a subject in need thereof by administering 1.9 mg/kg, 2.5 mg·kg, or 3.4 mg/kg of an anti-BCMA antibody; 15 mg/m$^2$, 20 mg/m$^2$, 27 mg/m$^2$, 36 mg/m$^2$, 45 mg/m$^2$, or 56 mg/m$^2$ of carfilzomib; and 20 mg or 40 mg of dexamethasone.

In one embodiment, the invention provides a method of treating cancer in a subject in need thereof by administering a therapeutically effective dose of a combination comprising an anti-BCMA antigen binding protein and ixazomib.

In one embodiment, the invention provides a method of treating cancer in a subject in need thereof by administering a therapeutically effective dose of a combination comprising an anti-BCMA antigen binding protein, ixazomib, and an anti-inflammatory compound.

In one embodiment, the invention provides a method of treating multiple myeloma in a subject in need thereof by administering a therapeutically effective dose of a combination comprising an anti-BCMA antibody, ixazomib and dexamethasone. In another embodiment, the invention provides a method of treating multiple myeloma in a subject in need thereof by administering 1.9 mg/kg, 2.5 mg·kg, or 3.4 mg/kg of an anti-BCMA antibody; 2.3 mg, 3 mg, or 4 mg of ixazomib; and 20 mg or 40 mg of dexamethasone.

In one embodiment, the invention provides a method of treating cancer in a subject in need thereof by administering a therapeutically effective dose of a combination comprising an anti-BCMA antigen binding protein and oprozomib.

In one embodiment, the invention provides a method of treating cancer in a subject in need thereof by administering a therapeutically effective dose of a combination comprising an anti-BCMA antigen binding protein, oprozomib, and an anti-inflammatory compound.

In one embodiment, the invention provides a method of treating multiple myeloma in a subject in need thereof by administering a therapeutically effective dose of a combination comprising an anti-BCMA antibody, oprozomib and dexamethasone.

In one embodiment, the invention provides a combination, as described herein, for use in therapy.

In one embodiment, the invention provides a combination, as described herein, for use in the treatment of cancer.

In one embodiment, the invention provides a combination, as described herein, for use in the treatment of cancer, wherein the combination comprises an anti-BCMA antigen binding protein and a proteasome inhibitor.

In one embodiment, the invention provides a combination, as described herein, for use in the treatment of cancer, wherein the combination comprises an anti-BCMA antigen binding protein, a proteasome inhibitor, and an anti-inflammatory compound.

In one embodiment, the invention provides a combination, as described herein, for use in the treatment of cancer, wherein the combination comprises an anti-BCMA antibody and a proteasome inhibitor, wherein the anti-BCMA antibody a CDRH1 comprising an amino acid sequence with at least 90%, 91%, 92%, 93%, 94%, 95%, 96%, 97%, 98%, 99% or 100% sequence identity to the amino acid sequence set forth in SEQ ID NO:1; a CDRH2 comprising an amino acid sequence with at least 90%, 91%, 92%, 93%, 94%, 95%, 96%, 97%, 98%, 99% or 100% sequence identity to the amino acid sequence set forth in SEQ ID NO:2; a CDRH3 comprising an amino acid sequence with at least 90%, 91%, 92%, 93%, 94%, 95%, 96%, 97%, 98%, 99% or 100% sequence identity to the amino acid sequence set forth in SEQ ID NO:3; a CDRL1 comprising an amino acid sequence with at least 90%, 91%, 92%, 93%, 94%, 95%, 96%, 97%, 98%, 99% or 100% sequence identity to the amino acid sequence set forth in SEQ ID NO:4; a CDRL2 comprising an amino acid sequence with at least 90%, 91%, 92%, 93%, 94%, 95%, 96%, 97%, 98%, 99% or 100% sequence identity to the amino acid sequence set forth in SEQ ID NO:5; and/or a CDRL3 comprising an amino acid sequence with at least 90%, 91%, 92%, 93%, 94%, 95%, 96%, 97%, 98%, 99% or 100% sequence identity to the amino acid sequence set forth in SEQ ID NO:6.

In one embodiment, the invention provides a combination, as described herein, for use in the treatment of cancer, wherein the combination comprises an anti-BCMA antibody and a proteasome inhibitor, wherein the anti-BCMA antibody comprises a VH comprising an amino acid sequence with at least 90%, 91%, 92%, 93%, 94%, 95%, 96%, 97%, 98%, 99% or 100% sequence identity to the amino acid sequence set forth in SEQ ID NO:7; and/or a VL comprising an amino acid sequence with at least 90%, 91%, 92%, 93%, 94%, 95%, 96%, 97%, 98%, 99% or 100% sequence identity to the amino acid sequence set forth in SEQ ID NO:8.

In one embodiment, the invention provides a combination, as described herein, for use in the treatment of cancer, wherein the combination comprises an anti-BCMA antibody and a proteasome inhibitor, wherein the anti-BCMA antibody has comprises a HC comprising an amino acid sequence with at least 90%, 91%, 92%, 93%, 94%, 95%, 96%, 97%, 98%, 99% or 100% sequence identity to the amino acid sequence set forth in SEQ ID NO:9; and/or a LC comprising an amino acid sequence with at least 90%, 91%, 92%, 93%, 94%, 95%, 96%, 97%, 98%, 99% or 100% sequence identity to the amino acid sequence set forth in SEQ ID NO:10.

In one embodiment, the invention provides a combination, as described herein, for use in the treatment of cancer, wherein the combination comprises an anti-BCMA antibody, a proteasome inhibitor, and an anti-inflammatory compound, wherein the anti-BCMA antibody a CDRH1 comprising an amino acid sequence with at least 90%, 91%, 92%, 93%, 94%, 95%, 96%, 97%, 98%, 99% or 100% sequence identity to the amino acid sequence set forth in SEQ ID NO:1; a CDRH2 comprising an amino acid sequence with at least 90%, 91%, 92%, 93%, 94%, 95%, 96%, 97%, 98%, 99% or 100% sequence identity to the amino acid sequence set forth in SEQ ID NO:2; a CDRH3 comprising an amino acid sequence with at least 90%, 91%, 92%, 93%, 94%, 95%, 96%, 97%, 98%, 99% or 100% sequence identity to the amino acid sequence set forth in SEQ ID NO:3; a CDRL1 comprising an amino acid sequence with at least 90%, 91%, 92%, 93%, 94%, 95%, 96%, 97%, 98%, 99% or 100% sequence identity to the amino acid sequence set forth in SEQ ID NO:4; a CDRL2 comprising an amino acid sequence with at least 90%, 91%, 92%, 93%, 94%, 95%, 96%, 97%, 98%, 99% or 100% sequence identity to the amino acid sequence set forth in SEQ ID NO:5; and/or a CDRL3 comprising an amino acid sequence with at least 90%, 91%, 92%, 93%, 94%, 95%, 96%, 97%, 98%, 99% or 100% sequence identity to the amino acid sequence set forth in SEQ ID NO:6.

In one embodiment, the invention provides a combination, as described herein, for use in the treatment of cancer, wherein the combination comprises an anti-BCMA antibody, a proteasome inhibitor, and an anti-inflammatory compound, wherein the anti-BCMA antibody has comprises a VH comprising an amino acid sequence with at least 90%, 91%, 92%, 93%, 94%, 95%, 96%, 97%, 98%, 99% or 100% sequence identity to the amino acid sequence set forth in SEQ ID NO:7; and/or a VL comprising an amino acid sequence with at least 90%, 91%, 92%, 93%, 94%, 95%, 96%, 97%, 98%, 99% or 100% sequence identity to the amino acid sequence set forth in SEQ ID NO:8.

In one embodiment, the invention provides a combination, as described herein, for use in the treatment of cancer, wherein the combination comprises an anti-BCMA antibody, a proteasome inhibitor, and an anti-inflammatory compound, wherein the anti-BCMA antibody comprises a HC comprising an amino acid sequence with at least 90%, 91%, 92%, 93%, 94%, 95%, 96%, 97%, 98%, 99% or 100% sequence identity to the amino acid sequence set forth in SEQ ID NO:9; and/or a LC comprising an amino acid sequence with at least 90%, 91%, 92%, 93%, 94%, 95%, 96%, 97%, 98%, 99% or 100% sequence identity to the amino acid sequence set forth in SEQ ID NO:10.

In one embodiment, the invention provides a combination, as described herein, for use in the treatment of cancer, wherein the combination comprises an anti-BCMA antigen binding protein and bortezomib.

In one embodiment, the invention provides a combination, as described herein, for use in the treatment of cancer, wherein the combination comprises an anti-BCMA antigen binding protein, bortezomib, and an anti-inflammatory compound.

In one embodiment, the invention provides a combination, as described herein, for use in the treatment of multiple myeloma, wherein the combination comprises an anti-BCMA antibody, bortezomib, and dexamethasone. In another embodiment, the invention provides a combination, as described herein, for use in the treatment of multiple myeloma, wherein the combination comprises 1.9 mg/kg, 2.5 mg/kg, or 3.4 mg/kg of anti-BCMA antibody; 1.3 mg/m$^2$ of bortezomib; and 20 mg or 40 mg dexamethasone.

In one embodiment, the invention provides a combination, as described herein, for use in the treatment of cancer, wherein the combination comprises an anti-BCMA antigen binding protein and carfilzomib.

In one embodiment, the invention provides a combination, as described herein, for use in the treatment of cancer, wherein the combination comprises an anti-BCMA antigen binding protein, carfilzomib, and an anti-inflammatory compound.

In one embodiment, the invention provides a combination, as described herein, for use in the treatment of multiple myeloma, wherein the combination comprises an anti-BCMA antibody, carfilzomib, and dexamethasone. In another embodiment, the invention provides a combination, as described herein, for use in the treatment of multiple myeloma, wherein the combination comprises 1.9 mg/kg, 2.5 mg/kg, or 3.4 mg/kg of anti-BCMA antibody; 15 mg/m$^2$, 20 mg/m$^2$, 27 mg/m$^2$, 36 mg/m$^2$, 45 mg/m$^2$, or 56 mg/m$^2$ of carfilzomib; and 20 mg or 40 mg dexamethasone.

In one embodiment, the invention provides a combination, as described herein, for use in the treatment of cancer, wherein the combination comprises an anti-BCMA antigen binding protein and ixazomib.

In one embodiment, the invention provides a combination, as described herein, for use in the treatment of cancer, wherein the combination comprises an anti-BCMA antigen binding protein, ixazomib, and an anti-inflammatory compound.

In one embodiment, the invention provides a combination, as described herein, for use in the treatment of multiple myeloma, wherein the combination comprises an anti-BCMA antibody, carfilzomib, and dexamethasone. In another embodiment, the invention provides a combination, as described herein, for use in the treatment of multiple myeloma, wherein the combination comprises 1.9 mg/kg, 2.5 mg/kg, or 3.4 mg/kg of anti-BCMA antibody; 2.3 mg, 3 mg, or 4 mg of ixazomib; and 20 mg or 40 mg dexamethasone.

In one embodiment, the invention provides a combination, as described herein, for use in the treatment of cancer, wherein the combination comprises an anti-BCMA antigen binding protein and oprozomib.

In one embodiment, the invention provides a combination, as described herein, for use in the treatment of cancer, wherein the combination comprises an anti-BCMA antigen binding protein, oprozomib, and an anti-inflammatory compound.

In one embodiment, provided is the use of a combination in the manufacture of a medicament for use in the treatment of cancer. In another embodiment, provided is the use of a combination in the manufacture of a medicament for use in the treatment of cancer, wherein the combination comprises an anti-BCMA antigen binding protein and a proteasome inhibitor. In yet another embodiment, provided is the use of a combination in the manufacture of a medicament for use in the treatment of cancer, wherein the combination comprises an anti-BCMA antigen binding protein, a proteasome inhibitor, and an anti-inflammatory compound.

Treatment Schedules

The appropriate treatment schedule of the anti-BCMA antigen binding protein, the proteasome inhibitor, and the anti-inflammatory compound will be determined readily by those of skill in the art.

In one exemplary treatment schedule, one dose of the anti-BCMA antigen binding protein is administered every 3 weeks (21 day cycle) for up to 16 cycles. In another exemplary treatment schedule, one dose of the anti-BCMA antigen binding protein is administered once weekly for three consecutive weeks followed by 1 week of rest (28-day cycle) for a maximum of 16 cycles. In yet another exemplary treatment schedule, one dose of anti-BCMA antigen binding protein is administered on day 1 of a 28-day cycle. In a further exemplary treatment schedule, one dose of anti-BCMA antigen binding protein is administered on day 1 of a 21-day cycle for up to 1 year.

In one exemplary embodiment, the proteasome inhibitor is bortezomib and the treatment schedule includes nine 6-week cycles and bortezomib is administered on days 1, 4, 8, 11, 22, 25, 29, and 32 on cycles 1 through 4 and on days 1, 8, 22, and 29 on cycles 5 through 9. In another exemplary embodiment, the proteasome inhibitor is bortezomib and the treatment schedule includes administration of a single dose of bortezomib on days 1, 4, 8, and 11 of a 21-day cycle for up to 8 cycles.

In one exemplary embodiment, the proteasome inhibitor is carfilzomib and the treatment schedule includes 28-day cycles where carfilzomib is administered on days 1, 2, 8, 9, 15 and 16 of each 28-day cycle. In another exemplary embodiment, the proteasome inhibitor is carfilzomib and the treatment schedule includes 28-day cycles where carfilzomib is administered on days 1, 2, 8, 9, 15 and 16 of cycles 1 through 12 and on days 1, 2, 15, and 16 on cycles 13 and beyond.

In one exemplary embodiment, the proteasome inhibitor is ixazomib and the treatment schedule includes 28-day cycles where ixazomib is administered on days 1, 8, and 15 of each 28-day cycle.

In one exemplary embodiment, the anti-inflammatory compound is dexamethasone and the treatment schedule includes administration of one dose of dexamethasone on days 1-4, 9-12, and 17-20 of a 28-day cycle. In another exemplary embodiment, the anti-inflammatory compound is dexamethasone and the treatment schedule includes administration of one dose of dexamethasone on days 1, 8, 15, and 22 of a 28-day cycle. In yet another embodiment, the anti-inflammatory compound is dexamethasone and the treatment schedule includes administration of dexamethasone on days 1, 2, 4, 5, 8, 9, 11, and 12 of a 21-day cycle. In yet another embodiment, the anti-inflammatory compound is dexamethasone and the treatment schedule includes administration of dexamethasone on days 1, 2, 8, 9, 15, 16, 22, and 23 of a 28-day cycle.

In one exemplary treatment schedule, the treatment schedules includes administration of 1.9 mg/kg, 2.5 mg/kg, or 3.4 mg/kg of an anti-BCMA antigen binding protein on day 1 of a 21-day cycle; administration of 1.3 mg/m$^2$ of bortezomib on days 1, 4, 8, and 11 of a 21-day cycle; and, optionally, administration of 20 mg or 40 mg of dexamethasone on days 1, 2, 4, 5, 8, 9, 11, and 12 of a 21-day cycle.

In one exemplary treatment schedule, the treatment schedules includes administration of 1.9 mg/kg, 2.5 mg/kg, or 3.4 mg/kg of an anti-BCMA antigen binding protein on day 1 of a 28-day cycle; administration of 15 mg/m$^2$, 20 mg/m$^2$, 27 mg/m$^2$, 36 mg/m$^2$, 45 mg/m$^2$, or 56 mg/m$^2$ of carfilzomib on days 1, 2, 8, 9, 15, and 16 of a 28-day cycle; and, optionally, administration of 20 mg or 40 mg of dexamethasone on days 1, 2, 8, 9, 15, 16, 22, 23, of a 28-day cycle.

In one exemplary treatment schedule, the treatment schedules includes administration of 1.9 mg/kg, 2.5 mg/kg, or 3.4 mg/kg of an anti-BCMA antigen binding protein on day 1 of a 28-day cycle; administration of 15 mg/m$^2$, 20 mg/m$^2$, 27 mg/m$^2$, 36 mg/m$^2$, 45 mg/m$^2$, or 56 mg/m$^2$ of carfilzomib on days 1, 2, 15, and 16 of a 28-day cycle; and, optionally, administration of 20 mg or 40 mg of dexamethasone on days 1, 2, 8, 9, 15, 16, 22, 23, of a 28-day cycle.

In one exemplary treatment schedule, the treatment schedules includes administration of 1.9 mg/kg, 2.5 mg/kg, or 3.4 mg/kg of an anti-BCMA antigen binding protein on day 1 of a 28-day cycle; administration of 2.3 mg, 3 mg, or 4 mg of ixazomib on days 1, 8, and 15 of a 28-day cycle; and, optionally, administration of 20 mg or 40 mg of dexamethasone on days 1, 8, 15, and 22 of a 28-day cycle.

Kits

In some aspects, the disclosure provides a kit for use in the treatment of cancer comprising:
  (i) an anti-BCMA antigen binding protein;
  (ii) a proteasome inhibitor; and
  iii) instructions for use in the treatment of cancer.

In some embodiments, the anti-BCMA antigen binding protein and the proteasome inhibitor are each individually formulated in their own pharmaceutical compositions with one or more pharmaceutically acceptable carriers.

In some aspects, the disclosure provides a kit for use in the treatment of cancer comprising:
  (i) an anti-BCMA antigen binding protein;
  (ii) a proteasome inhibitor;
  (iii) anti-inflammatory compound; and
  (iii) instructions for use in the treatment of cancer.

In some embodiments, the anti-BCMA antigen binding protein, the proteasome inhibitor, and the anti-inflammatory compound are each individually formulated in their own pharmaceutical compositions with one or more pharmaceutically acceptable carriers.

In some aspects, the disclosure provides a kit for use in the treatment of cancer comprising:
  (i) an anti-BCMA antigen binding protein;
  (ii) instructions for use in the treatment of cancer when combined with a proteasome inhibitor.

In some aspects, the disclosure provides a kit for use in the treatment of cancer comprising:
  (i) an anti-BCMA antigen binding protein;
  (ii) instructions for use in the treatment of cancer when combined with a proteasome inhibitor and an anti-inflammatory compound.

EXAMPLES

Example 1: Treatment of Multiple Myeloma with an Anti-BCMA Antibody Drug Conjugate, Bortezomib, and Dexamethasone A Phase I/II study is conducted in human subjects to determine safety, tolerability, and to determine the recommended Phase 2 dose (RP2D) of an anti-BCMA antigen binding protein given in combination with bortezomib plus dexamethasone in subjects with relapsed/refractory multiple myeloma (RRMM), and to evaluate safety and clinical activity of the RP2D combination treatments in participants with RRMM.

The anti-BCMA antigen binding protein is an anti-BCMA antibody comprising a CDRH1 comprising the amino acid sequence set forth in SEQ ID NO:1; a CDRH2 comprising the amino acid sequence set forth in SEQ ID NO:2; a CDRH3 comprising the amino acid sequence set forth in SEQ ID NO:3; a CDRL1 comprising the amino acid sequence set forth in SEQ ID NO:4; a CDRL2 comprising the amino acid sequence set forth in SEQ ID NO:5; and the CDRL3 comprising an amino acid sequence set forth in SEQ ID NO:6; and is conjugated to monomethyl auristatin F (MMAF) as described in Tai et al Blood. 2014 May 15; 123(20): 3128-3138.

A single treatment cycle consists of 21 days. Subjects not experiencing dose-limiting or intolerable adverse events may continue treatment for up to 1 year.

The study consists of two parts: Part 1 is a dose escalation study and Part 2 is a dose expansion study.

Study Part 1 is a Dose Escalation phase to evaluate the safety and tolerability of combination dose levels. It is designed to identify the Recommended Phase 2 Dose (RP2D) Dose level of the anti-BCMA antigen binding protein in combination with bortezomib plus dexamethasone. Subjects are initially tested at 2.5 mg/kg of the anti-BCMA antigen binding protein on Day 1 of the 21-day cycle; 1.3 mg/m2 of bortezomib on days 1, 4, 8, and 11 of the 21-day cycle; and 20 mg dexamethasone on days 1, 2, 4, 5, 8, 9, 11, and 12 of the 21-day cycle.

After Cycle 1 is completed the dose of the anti-BCMA antigen binding protein could be adjusted to 1.9 mg/kg or 3.4 mg/kg.

A summary of the treatment schedule is provided in Table 1:

TABLE 1

Treatment schedule

| RRMM Patients | Anti-BCMA antigen binding protein | Bortezomib | Dexamethasone |
| --- | --- | --- | --- |
| Dosage levels: | 1.9 mg/kg, 2.5 mg/kg, or 3.4 mg/kg | 1.3 mg/m² | 20 mg |
| Dosing Regimen | Day 1 of 21-day Cycle | Days 1, 4, 8, and 11 of 21-day cycle | Days 1, 2, 4, 5, 8, 9, 11, and 12 of 21-day cycle |

In Part 2 (Dose Expansion) additional subjects are enrolled and treated at the RP2D for each of the anti-BCMA antigen binding protein, bortezomib, and dexamethasone. Safety (AE, ECGs, MM symptoms, and Laboratory assessments), clinical response and changes in symptoms/quality of life are evaluated at the end of Cycle 1 and all subsequent cycles.

SEQUENCE LISTINGS

SEQ. ID. NO. 1-CDRH1
NYWMH

SEQ. ID. NO. 2: CDRH2
ATYRGHSDTYYNQKFKG

SEQ. ID. NO. 3: CDRH3
GAIYDGYDVLDN

SEQ. ID. NO. 4: CDRL1
SASQDISNYLN

SEQ. ID. NO. 5: CDRL2
YTSNLHS

SEQ. ID. NO. 6: CDRL3
QQYRKLPWT

SEQ. ID. NO. 7: heavy chain variable region
QVQLVQSGAEVKKPGSSVKVSCKASGGTFSNYWMHWVRQAPGQGLEWM
GATYRGHSDTYYNQKFKGRVTITADKSTSTAYMELSSLRSEDTAVYYC
ARGAIYDGYDVLDNWGQGTLVTVSS SED. ID. NO. 8: light chain variable region
DIQMTQSPSSLSASVGDRVTITCSASQDISNYLNWYQQKPGKAPKLLI
YYTSNLHSGVPSRFSGSGSGTDFTLTISSLQPEDFATYYCQQYRKLPW
TFGQGTKLEIKR SEQ. ID. NO. 9: heavy chain region
QVQLVQSGAEVKKPGSSVKVSCKASGGTFSNYWMHWVRQAPGQGLEWM
GATYRGHSDTYYNQKFKGRVTITADKSTSTAYMELSSLRSEDTAVYYC
ARGAIYDGYDVLDNWGQGTLVTVSSASTKGPSVFPLAPSSKSTSGGTA
ALGCLVKDYFPEPVTVSWNSGALTSGVHTFPAVLQSSGLYSLSSVVTV
PSSSLGTQTYICNVNHKPSNTKVDKKVEPKSCDKTHTCPPCPAPELLG
GPSVFLFPPKPKDTLMISRTPEVTCVVVDVSHEDPEVKFNWYVDGVEV
HNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVE
WESNGQPENNYKTTPPVLDSDGSFFLYSKLTVDKSRWQQGNVFSCSVM
HEALHNHYTQKSLSLSPGK SEQ. ID. NO. 10: light chain region
DIQMTQSPSSLSASVGDRVTITCSASQDISNYLNWYQQKPGKAPKLLI
YYTSNLHSGVPSRFSGSGSGTDFTLTISSLQPEDFATYYCQQYRKLPW
TFGQGTKLEIKRTVAAPSVFIFPPSDEQLKSGTASVVCLLNNFYPREA
KVQWKVDNALQSGNSQESVTEQDSKDSTYSLSSTLTLSKADYEKHKVY
ACEVTHQGLSSPVTKSFNRGEC

The invention claimed is:

1. A method of treating primary amyloidosis (AL) in a subject in need thereof, the method comprising: administering to the subject in need thereof a dose of 1.9 mg/kg or 2.5 mg/kg of an anti-B-cell maturation antigen (BCMA) antibody conjugated to monomethyl auristatin F (MMAF), wherein the anti-BCMA antibody comprises a heavy chain comprising the amino acid sequence set forth in SEQ ID NO:9 and a light chain comprising the amino acid sequence set forth in SEQ ID NO:10.

2. The method of claim 1, wherein 1.9 mg/kg of the anti-BCMA antibody conjugated to MMAF is administered to the subject in need thereof.

3. The method of claim 1, wherein 2.5 mg/kg of the anti-BCMA antibody conjugated to MMAF is administered to the subject in need thereof.

4. The method of claim 1 further comprising administering to the subject in need thereof a proteasome inhibitor.

5. The method of claim 4, wherein the proteasome inhibitor is bortezomib.

6. The method of claim 5, wherein 1.3 mg/m² bortezomib is administered to the subject in need thereof.

7. The method of claim 6, wherein 1.3 mg/m² bortezomib is administered to the subject in need thereof on days 1, 4, 8, and 11 of a 21-day cycle.

8. The method of claim 4, wherein the proteasome inhibitor is carfilzomib.

9. The method of claim 4, wherein the proteasome inhibitor is ixazomib.

10. The method of claim 4, wherein the proteasome inhibitor is oprozomib.

11. A method of treating primary amyloidosis (AL) in a subject in need thereof, the method comprising: administering to the subject in need thereof (a) a dose of 1.9 mg/kg or 2.5 mg/kg of an anti-B-cell maturation antigen (BCMA) antibody conjugated to monomethyl auristatin F (MMAF), wherein the anti-BCMA antibody comprises a heavy chain comprising the amino acid sequence set forth in SEQ ID NO:9 and a light chain comprising the amino acid sequence set forth in SEQ ID NO:10, (b) a proteasome inhibitor, and (c) an anti-inflammatory compound.

12. The method of claim 11, wherein 1.9 mg/kg of the anti-BCMA antibody conjugated to MMAF is administered to the subject in need thereof.

13. The method of claim 11, wherein 2.5 mg/kg of the anti-BCMA antibody conjugated to MMAF is administered to the subject in need thereof.

14. The method of claim 11, wherein the proteasome inhibitor is bortezomib.

15. The method of claim 14, wherein 1.3 mg/m² of bortezomib is administered to the subject in need thereof.

16. The method of claim 15, wherein 1.3 mg/m² of bortezomib is administered to the subject in need thereof on days 1, 4, 8, and 11 of a 21-day cycle.

17. The method of claim 11, wherein the anti-inflammatory compound is dexamethasone.

18. The method of claim 17, wherein 20 mg or 40 mg of dexamethasone is administered to the subject in need thereof.

19. The method of claim 18, wherein 20 mg or 40 mg of dexamethasone is administered to the subject in need thereof on days 1, 2, 4, 5, 8, 9, 11, and 12 of a 21-day cycle.

* * * * *

UNITED STATES PATENT AND TRADEMARK OFFICE
CERTIFICATE OF CORRECTION

| | | |
|---|---|---|
| PATENT NO. | : 12,234,293 B2 | Page 1 of 1 |
| APPLICATION NO. | : 17/846950 | |
| DATED | : February 25, 2025 | |
| INVENTOR(S) | : Khandekar et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 156 days.

Signed and Sealed this
Twenty-ninth Day of July, 2025

Coke Morgan Stewart
*Acting Director of the United States Patent and Trademark Office*

SEQUENCE LISTING

```
<160> NUMBER OF SEQ ID NOS: 10

<210> SEQ ID NO 1
<211> LENGTH: 5
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 1

Asn Tyr Trp Met His
1               5

<210> SEQ ID NO 2
<211> LENGTH: 17
<212> TYPE: PRT
<213> ORGANISM: Artificial Sequence
<220> FEATURE:
```

<223> OTHER INFORMATION: /note="Description of Artificial Sequence:
      Synthetic peptide"

<400> SEQUENCE: 2

Ala Thr Tyr Arg Gly His Ser Asp Thr Tyr Tyr Asn Gln Lys Phe Lys
1               5                   10                  15

Gly

<210> SEQ ID NO 3
<211> LENGTH: 12
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 3

Gly Ala Ile Tyr Asp Gly Tyr Asp Val Leu Asp Asn
1               5                   10

<210> SEQ ID NO 4
<211> LENGTH: 11
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 4

Ser Ala Ser Gln Asp Ile Ser Asn Tyr Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 5

Tyr Thr Ser Asn Leu His Ser
1               5

<210> SEQ ID NO 6
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 6

Gln Gln Tyr Arg Lys Leu Pro Trp Thr
1               5

<210> SEQ ID NO 7
<211> LENGTH: 121
<212> TYPE: PRT
<213> ORGANISM: Artificial Sequence
<220> FEATURE:
<223> OTHER INFORMATION: /note="Description of Artificial Sequence:
      Synthetic polypeptide"

<400> SEQUENCE: 7

Gln Val Gln Leu Val Gln Ser Gly Ala Glu Val Lys Lys Pro Gly Ser
1               5                   10                  15

```
Ser Val Lys Val Ser Cys Lys Ala Ser Gly Gly Thr Phe Ser Asn Tyr
            20                  25                  30

Trp Met His Trp Val Arg Gln Ala Pro Gly Gln Gly Leu Glu Trp Met
        35                  40                  45

Gly Ala Thr Tyr Arg Gly His Ser Asp Thr Tyr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ile Tyr Asp Gly Tyr Asp Val Leu Asp Asn Trp Gly
            100                 105                 110

Gln Gly Thr Leu Val Thr Val Ser Ser
        115                 120

<210> SEQ ID NO 8
<211> LENGTH: 108
<212> TYPE: PRT
<213> ORGANISM: Artificial Sequence
<220> FEATURE:
<223> OTHER INFORMATION: /note="Description of Artificial Sequence:
      Synthetic polypeptide"

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Arg Lys Leu Pro Trp
                85                  90                  95

Thr Phe Gly Gln Gly Thr Lys Leu Glu Ile Lys Arg
            100                 105

<210> SEQ ID NO 9
<211> LENGTH: 451
<212> TYPE: PRT
<213> ORGANISM: Artificial Sequence
<220> FEATURE:
<223> OTHER INFORMATION: /note="Description of Artificial Sequence:
      Synthetic polypeptide"

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Trp Met His Trp Val Arg Gln Ala Pro Gly Gln Gly Leu Glu Trp Met
        35                  40                  45

Gly Ala Thr Tyr Arg Gly His Ser Asp Thr Tyr Tyr Asn Gln Lys Phe
    50                  55                  60

Lys Gly Arg Val Thr Ile Thr Ala Asp Lys Ser Thr Ser Thr Ala Tyr
65                  70                  75                  80
```

Met Glu Leu Ser Ser Leu Arg Ser Glu Asp Thr Ala Val Tyr Tyr Cys
                85                  90                  95

Ala Arg Gly Ala Ile Tyr Asp Gly Tyr Asp Val Leu Asp Asn Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 10
<211> LENGTH: 214
<212> TYPE: PRT
<213> ORGANISM: Artificial Sequence
<220> FEATURE:

<223> OTHER INFORMATION: /note="Description of Artificial Sequence:
      Synthetic polypeptide"

<400> SEQUENCE: 10

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Arg Lys Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```